(12) United States Patent
Richter et al.

(10) Patent No.: US 11,583,398 B2
(45) Date of Patent: Feb. 21, 2023

(54) MODULAR PERCUTANEOUS VALVE STRUCTURE AND DELIVERY METHOD

(71) Applicant: Valve Medical Ltd., Tel Aviv (IL)

(72) Inventors: Yoram Richter, Ramat Hasharon (IL); Jacob Richter, Arsuf (IL)

(73) Assignee: Valve Medical Ltd., Tel Aviv (IL)

( * ) Notice: Subject to any disclaimer, the term of this patent is extended or adjusted under 35 U.S.C. 154(b) by 400 days.

(21) Appl. No.: 16/691,860

(22) Filed: Nov. 22, 2019

(65) Prior Publication Data
US 2020/0085574 A1    Mar. 19, 2020

Related U.S. Application Data

(60) Division of application No. 15/195,108, filed on Jun. 28, 2016, now Pat. No. 10,517,718, which is a continuation of application No. 12/686,335, filed on Jan. 12, 2010, now Pat. No. 9,402,720.

(60) Provisional application No. 61/144,007, filed on Jan. 12, 2009.

(51) Int. Cl.
*A61F 2/24*    (2006.01)

(52) U.S. Cl.
CPC .......... *A61F 2/2418* (2013.01); *A61F 2/2409* (2013.01); *A61F 2/2412* (2013.01); *A61F 2/2439* (2013.01); *A61F 2220/0033* (2013.01); *A61F 2230/0091* (2013.01); *A61F 2250/0004* (2013.01); *A61F 2250/006* (2013.01); *A61F 2250/0008* (2013.01); *Y10T 29/49826* (2015.01)

(58) Field of Classification Search
CPC .... A61F 2/2418; A61F 2/2409; A61F 2/2412; A61F 2/2439; A61F 2220/0033; A61F 2230/0091; A61F 2250/0004; A61F 2250/006
See application file for complete search history.

(56) References Cited

U.S. PATENT DOCUMENTS

| | | | |
|---|---|---|---|
| 5,800,531 A * | 9/1998 | Cosgrove | A61F 2/2412 623/2.11 |
| 9,402,720 B2 * | 8/2016 | Richter | A61F 2/2418 |
| 2002/0138138 A1 * | 9/2002 | Yang | A61F 2/2412 623/2.38 |
| 2004/0024451 A1 * | 2/2004 | Johnson | A61F 2/2412 623/2.11 |

(Continued)

*Primary Examiner* — Alexander J Orkin
(74) *Attorney, Agent, or Firm* — Cadwalader, Wickersham & Taft LLP

(57) ABSTRACT

A modular prosthetic valve device for implantation in a patient and a system for and method of delivering such a modular valve device and assembling it in vivo are disclosed. The valve device is designed as two or more modules to be delivered unassembled, spatially separate, and combined into an assembled valve device in the body at or near the site of implantation. The valve device of the invention is deliverable as modules, providing a smaller delivery diameter than pre-assembled percutaneous valves, permitting use of a delivery device of reduced diameter, and increasing the flexibility of the valve device during delivery, compared to percutaneous valve devices in the art. The modules of the valve device may be connected by pull wires for delivery sequentially, and then assembled by remote manipulation using the pull wires. Various locking mechanisms are provided for attaching the device modules together.

14 Claims, 18 Drawing Sheets

(56) References Cited

U.S. PATENT DOCUMENTS

| | | | |
|---|---|---|---|
| 2005/0137699 A1* | 6/2005 | Salahieh | A61F 2/2418 623/2.11 |
| 2006/0195180 A1* | 8/2006 | Kheradvar | A61F 2/2427 623/2.11 |
| 2006/0195186 A1* | 8/2006 | Drews | A61F 2/2412 623/2.38 |
| 2007/0016288 A1* | 1/2007 | Gurskis | A61F 2/2418 623/2.11 |
| 2007/0265701 A1* | 11/2007 | Gurskis | A61F 2/2439 623/2.4 |
| 2008/0200980 A1* | 8/2008 | Robin | A61F 2/2418 623/2.11 |
| 2009/0222082 A1* | 9/2009 | Lock | A61F 2/2409 623/2.11 |

* cited by examiner

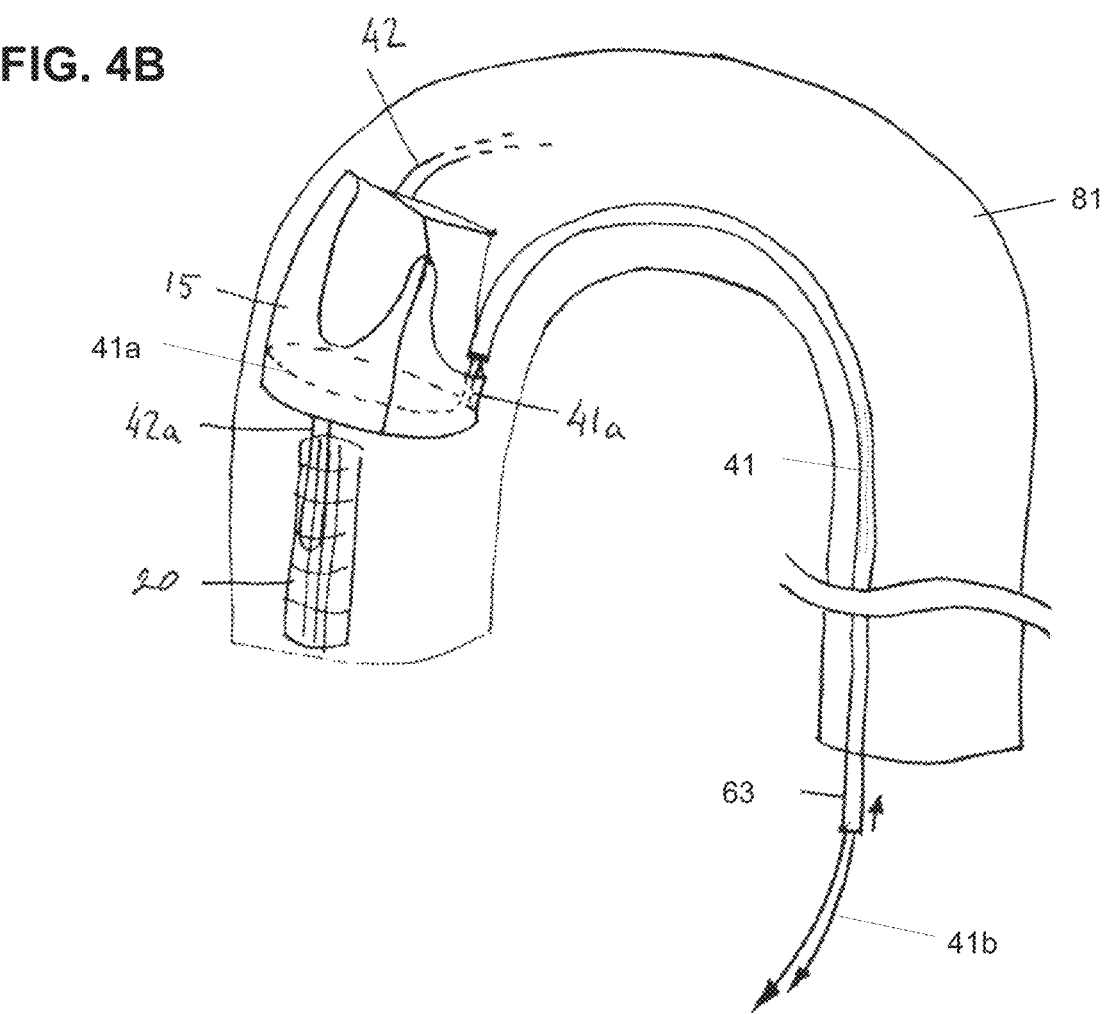

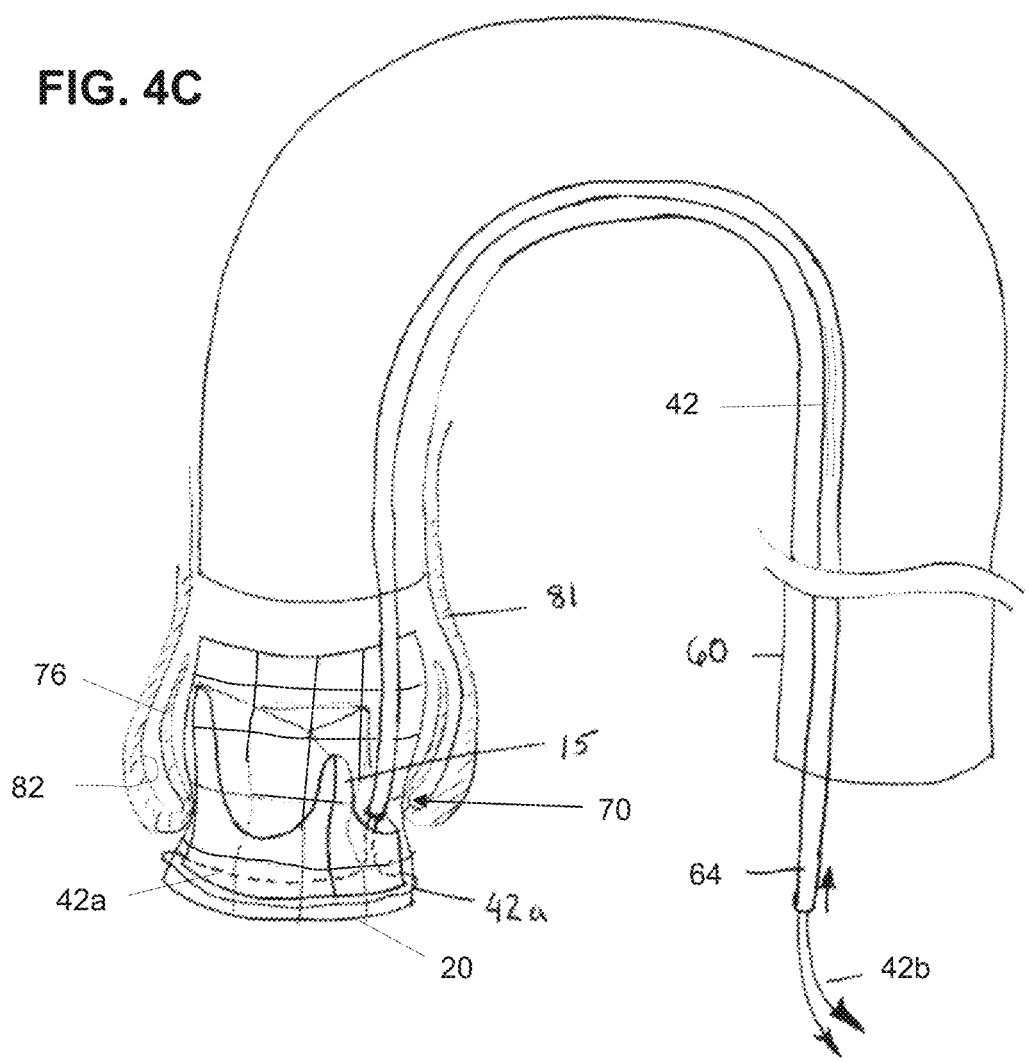

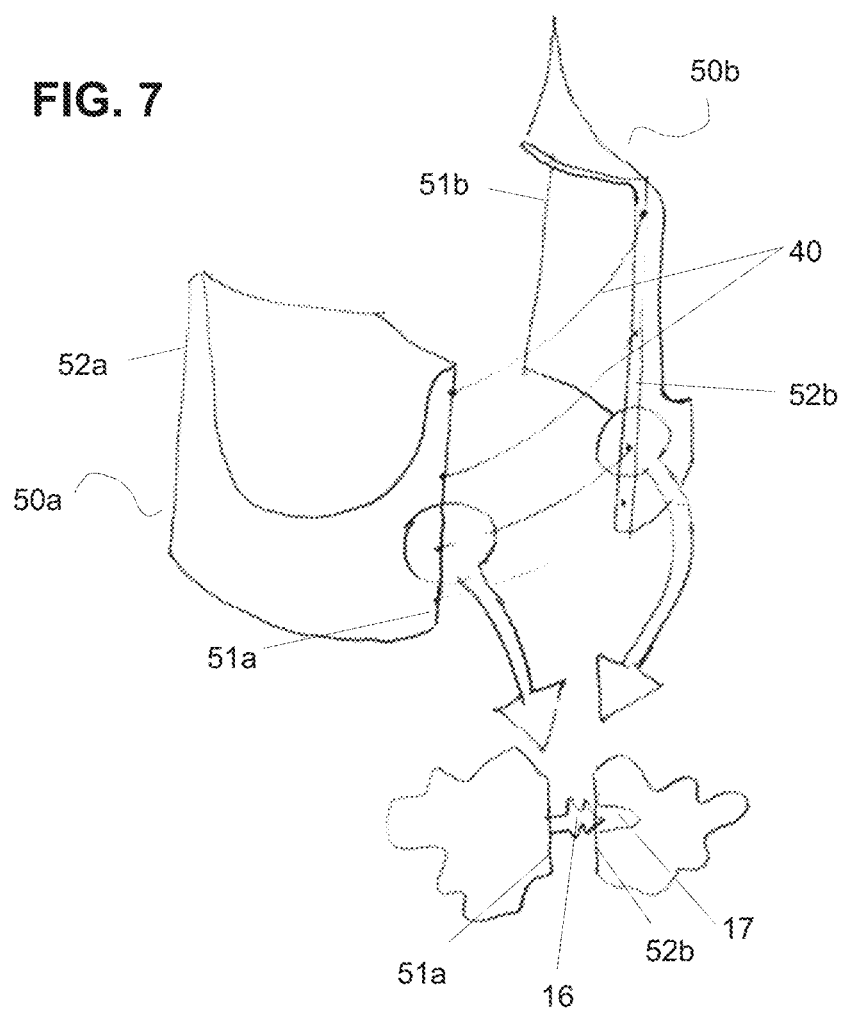

FIG. 8A
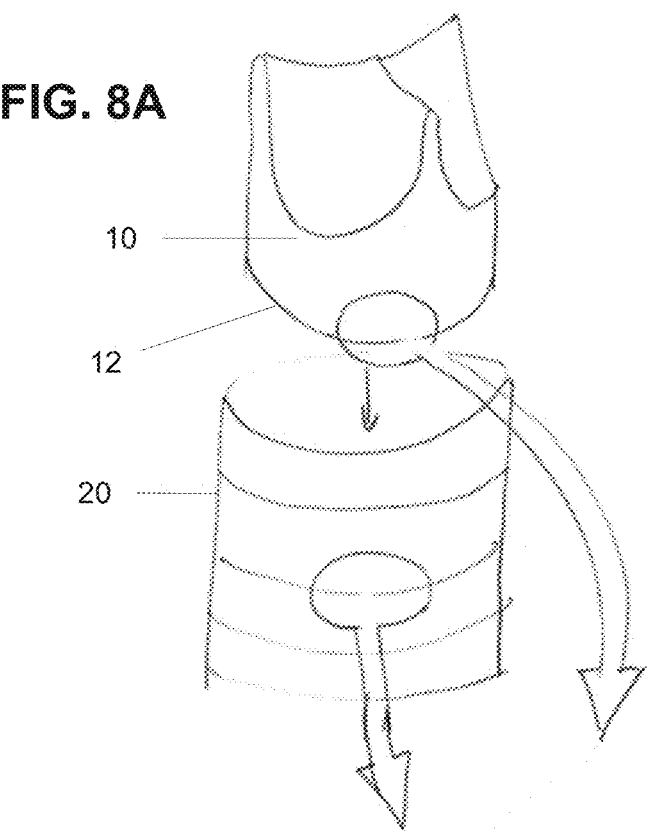
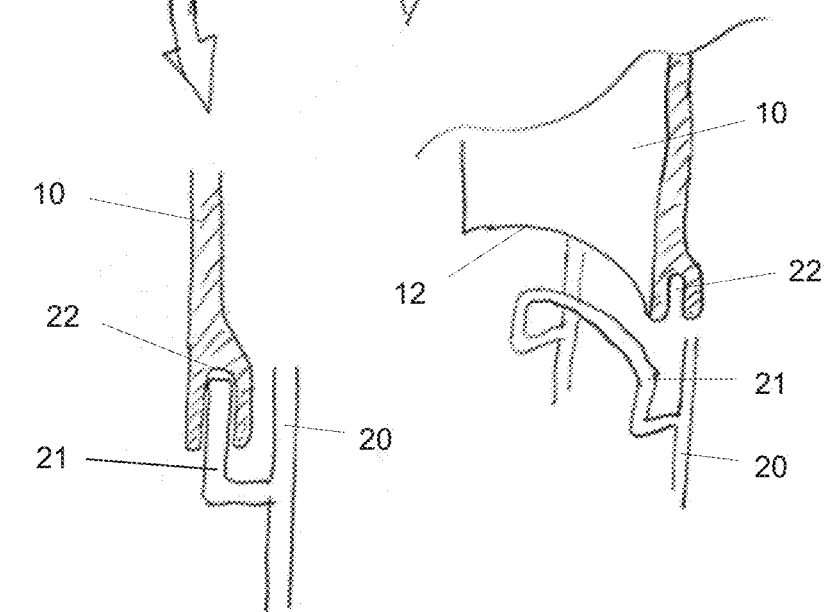
FIG. 8C  FIG. 8B

FIG. 10A
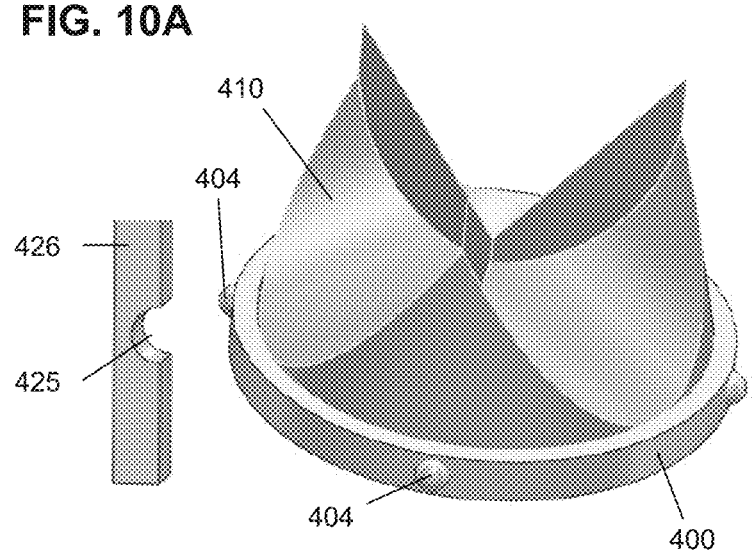
FIG. 10B
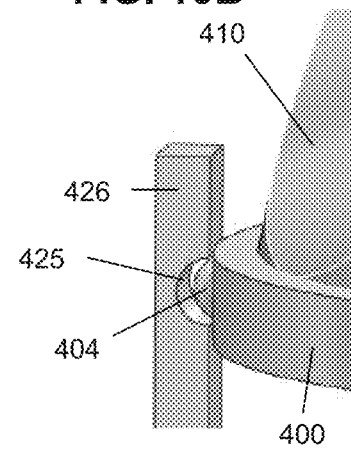
FIG. 10C      FIG. 10C'
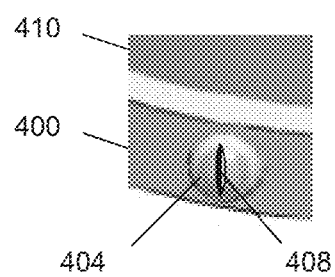  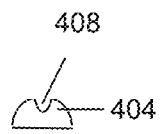
FIG. 10D  FIG. 10D'
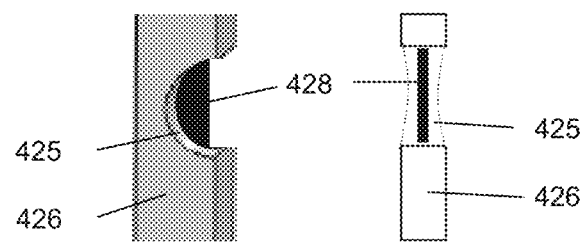

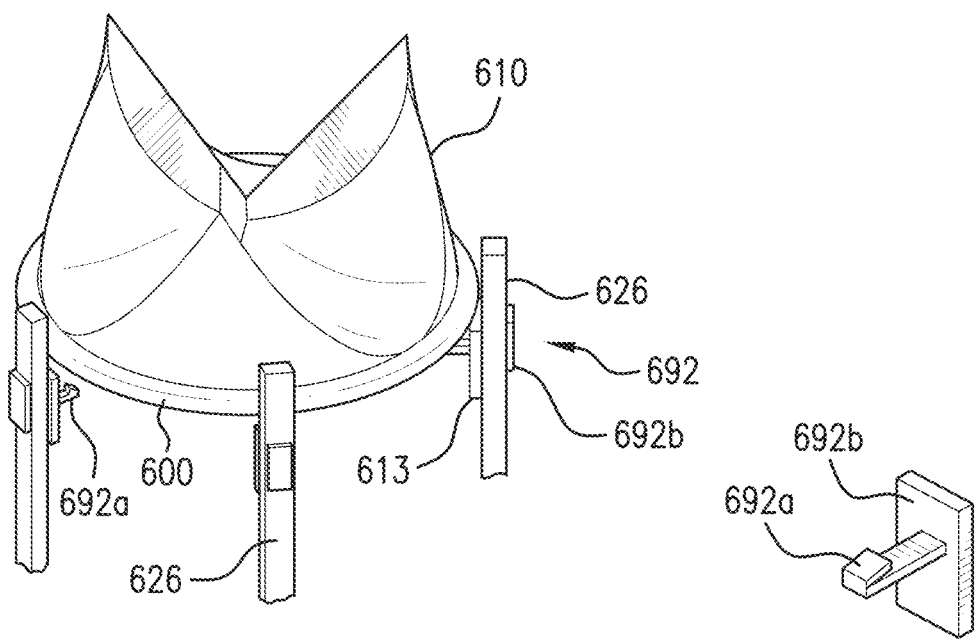
FIG.12A
FIG.12A'
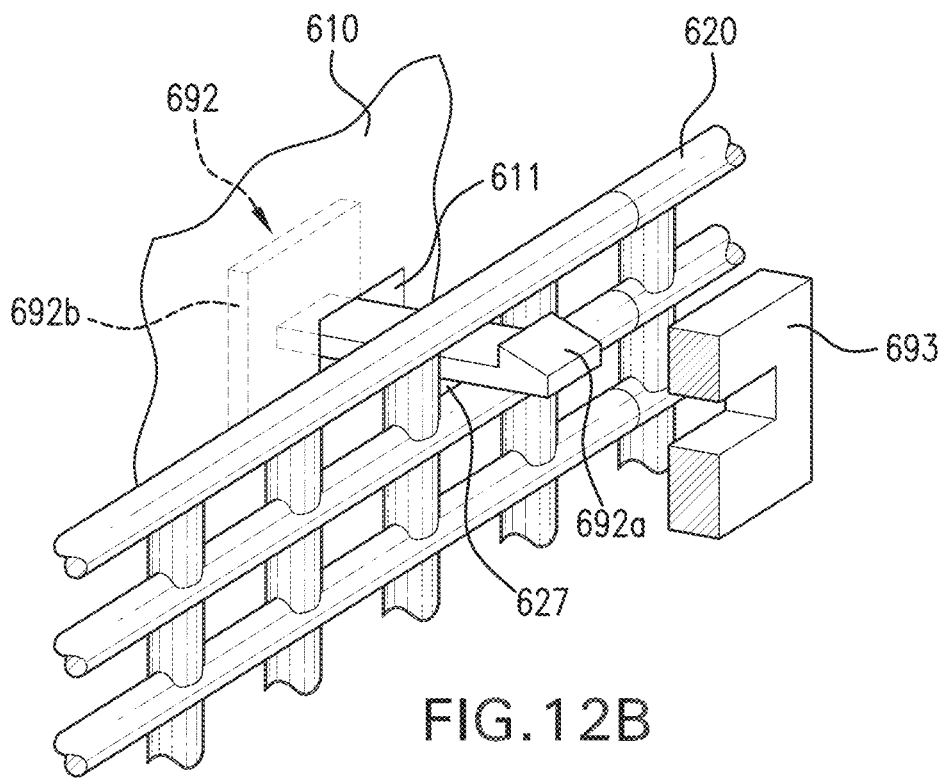
FIG.12B

FIG. 13A
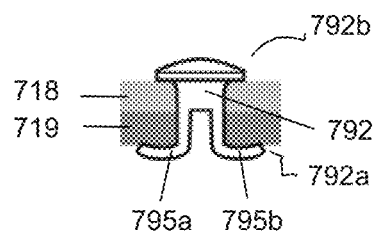
FIG. 13B
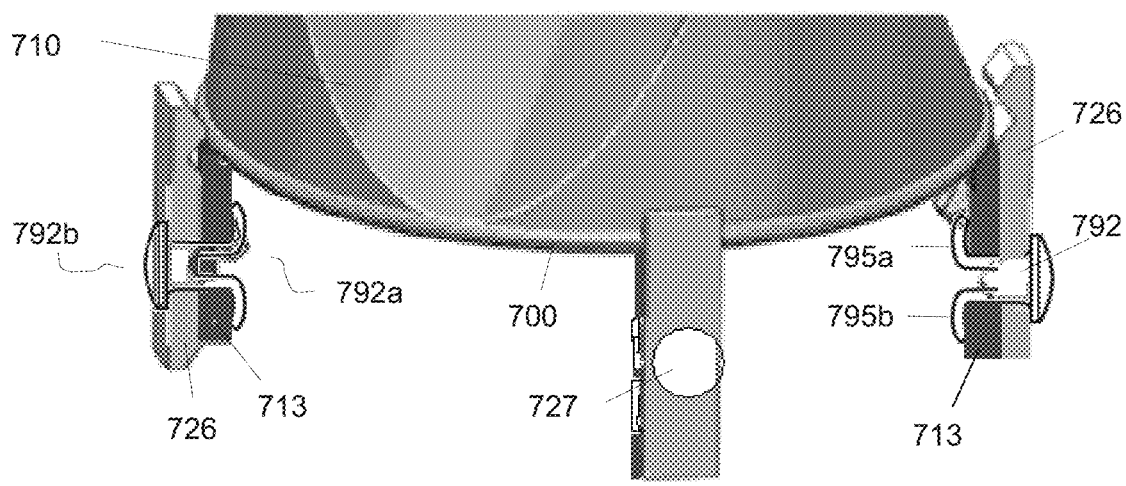
FIG. 13C   FIG. 13D   FIG. 13E
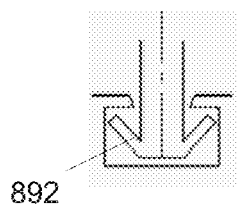 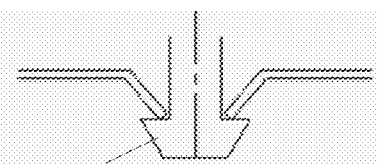 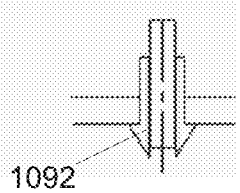

MODULAR PERCUTANEOUS VALVE STRUCTURE AND DELIVERY METHOD

This application is a divisional of U.S. patent application Ser. No. 15/195,108 filed Jun. 28, 2016, which is a continuation of U.S. patent application Ser. No. 12/686,335 filed Jan. 12, 2010 and issued as U.S. Pat. No. 9,402,720 on Aug. 2, 2016, and claims the benefit of priority of U.S. Provisional Application Ser. No. 61/144,007, filed Jan. 12, 2009, all of which are incorporated herein by reference in their entirety.

FIELD OF INVENTION

The present invention relates to prosthetic valve devices for implantation in the body and methods of deployment thereof. In particular, the invention relates to a multi-component, or modular, percutaneous prosthetic valve device—a prosthetic valve capable of being delivered in parts and assembled in the body, and therefore capable of having a smaller delivery diameter than fully assembled percutaneous valve devices. The invention also relates to a system comprising such a modular valve device and a delivery device having a reduced diameter compared to a delivery device for a fully assembled percutaneous valve device, and a method of delivering and deploying such a modular valve device using the reduced diameter delivery device system. The invention further relates to a method of assembling a modular valve device including locking the device modules together using locking mechanisms.

BACKGROUND OF THE INVENTION

The human body contains a wide variety of natural valves, such as, for example, heart valves, esophageal and stomach valves, intestinal valves, and valves within the lymphatic system. Natural valves can degenerate for a variety of reasons, such as disease, age, and the like. A malfunctioning valve fails to maintain the bodily fluid flow in a single direction with minimal pressure loss. An example of a malfunctioning valve is a heart valve that may be either stenotic, i.e., the leaflets of the valve do not open fully, or regurgitant, i.e., the leaflets of the valve do not close properly. It is desirable to restore valve function to regain the proper functioning of the organ with which the valve is associated. For example, proper valve function in the heart ensures that blood flow is maintained in a single direction through a valve with minimal pressure loss, so that blood circulation and pressure can be maintained. Similarly, proper esophageal valve function ensures that acidic gastric secretions do not irritate or permanently damage the esophageal lining.

Several percutaneous prosthetic valve systems have been described. One example described in Andersen, et. al. (U.S. Pat. No. 5,411,552) comprises an expandable stent and a collapsible valve which is mounted onto the stent prior to deployment. The collapsible valve may be a biological valve or it may be made of synthetic material. The Anderson prosthetic valve is delivered and deployed using a balloon catheter which balloon is used to expand the valve-stent prosthesis to its final size. See also, U.S. Pat. No. 6,168,614 (Andersen, et al.) entitled "Valve Prosthesis for Implantation in the Body" and U.S. Pat. No. 5,840,081 (Andersen, et al.) entitled "System and Method for Implanting Cardiac Valves."

Spenser, et. al. (U.S. Pat. No. 6,893,460) describe another prosthetic valve device comprising a valve structure made of biological or synthetic material and a supporting structure, such as a stent. The Spenser prosthetic valve is a crimpable leafed-valve assembly consisting of a conduit having an inlet and an outlet, made of pliant material arranged to present collapsible walls at the outlet. The valve assembly is affixed to the support stent prior to deployment. The complete valve device is deployed at a target location within the body duct using a deploying means, such as a balloon catheter or a similar device.

Percutaneous implantation of prosthetic valves is safer, cheaper, and provides shorter patient recovery time than standard surgical procedures. However, current artificial percutaneous prosthetic valves have the disadvantage of being extremely bulky, even when compressed for delivery. The problem with this bulkiness is that it requires the delivery catheter to have a rather large diameter. Large catheters generally are not suitable for percutaneous procedures and require cut-down procedures and a surgeon and/or sophisticated and difficult puncture-closure techniques. The bulkiness and large diameter of current valve devices and delivery systems combined with the anatomy through which the devices must be delivered also can make delivery into the lumen problematic from the point of view of success rate, accuracy of deployment, and risk of complications. Specifically, delivery complications may arise due to the shape of the lumen, for example, the significant natural curve of the aortic arch and/or a tortuous iliac/femoral artery through which the catheter is introduced. Further, a catheter of such diameter tends to be less flexible than a smaller diameter catheter, especially when loaded with a bulky, inflexible device, and manipulating such a loaded catheter through a narrow vessel and in particular a curved vessel substantially raises the potential for damage to that vessel wall.

Accurate placement of current percutaneous valve devices relative to the existing native anatomy is often problematic, particularly in the case of aortic valve replacements. A prosthetic valve that is placed too distally (i.e., toward the aorta) can occlude or impede flow into the orifices of the coronary arteries. For example, depending on the position of the coronary ostia, either the skirt of the prosthetic valve or large native valve leaflets pressed down against the aorta wall may physically or functionally obstruct the orifices and impede coronary arterial flow. See, e.g., Piazza, N., et al., "Anatomy of the Aortic Valvar Complex and Its Implications for Transcatheter Implantation of the Aortic Valve," CIRCULATION CARDIOVASCULAR INTERVENTIONS, 1:74-81 (2008); Webb, J G, et al., "Percutaneous aortic valve implantation retrograde from the femoral artery," CIRCULATION, 113:842-850 (2006). This obstruction may be either physical or it may be functional, i.e. the orifices of the coronary arteries are physically patent, but due to alterations in flow patterns produced by the prosthetic valve, flow into the coronary arteries is partially compromised. A prosthetic valve that is placed too proximally (i.e., toward the ventricular outflow tracts of the left ventricle) can interfere with the anterior leaflet of the Mitral valve, the atrioventricular node, or the bundle of His (conduction tissues). Approximately thirty percent of patients receiving prosthetic valves percutaneously require pacemakers, because the valve is placed with the ventricular end too close to or on top of the left bundle branch, putting pressure on the electrical conduction apparatus. See, e.g., Piazza, N., et al., "Early and persistent intraventricular conduction abnormalities and requirements for pacemaking following percutaneous replacement of the aortic valve," JACC CARDIOVASCULAR INTERVENTIONS, 1:310-316 (2008); Piazza, N., et al., "Anatomy of the Aortic Valvar Complex and Its Implications for Transcatheter Implantation of the Aortic Valve," CIRCULATION CARDIOVASCULAR INTERVENTIONS, 1:74-81 (2008).

Therefore, a need exists to facilitate the delivery of artificial valves and also to increase the safety of the procedure. A valve device having a smaller delivery diameter than pre-assembled percutaneous valve devices and that can be delivered through vessel without incurring further damage to the wall of the body lumen is highly desirable.

SUMMARY OF THE INVENTION

The present invention relates to a multi-component, or modular, percutaneous valve device and system and a method of delivering a prosthetic valve device in parts and of assembling the modular valve device within the body.

The present invention provides a modular percutaneous prosthetic valve device that is minimally invasive, a system comprising such a device, and a method of percutaneous valve delivery.

The modular prosthetic valve device comprises a plurality of device modules for delivery. In one embodiment, the plurality of device modules includes a valve module and a support structure, which are designed to be combined into the assembled valve device in the body. The valve module is the portion of the valve device having the leaflets and once assembled it provides a conduit having an inlet end and an outlet end. The valve module may itself comprise a plurality of device modules. Thus, in one embodiment, the valve module may further comprise a plurality of valve sections, which may be assembled in vivo to form a valve assembly. The valve assembly may then be combined with the support structure into the assembled valve device. In another embodiment, the plurality of device modules may include a plurality of valve sections that may be deployed and assembled into a valve assembly and implanted without a support structure. Alternatively, individual valve sections may be implanted, for example, where a native leaflet is diseased.

The system of the invention comprises a modular prosthetic valve device and a delivery device for delivering the valve device to the desired location in a body lumen. The system may also comprise arrangements to adjustably connect the valve module to the support structure and/or the support structure to anchor points. The system of the present invention may further comprise a temporary valve.

The present invention also relates to a method of delivering a modular valve device to a body lumen in need of a valve and a method of assembling the modular valve device within a lumen. Various methods may be used to deliver the device modules to a desired location for assembly in the body. The method includes percutaneously introducing a valve not as a whole, but in parts (modules) via a delivery device, such as a catheter. These parts may include a support structure and a valve module. The valve module may be a one piece valve component or it may be a valve assembly comprising multiple parts. The device modules may be assembled either sequentially at the site of implantation, or at a site different from the site of implantation (and then implanted). The device modules may be assembled and implanted in any order that suits the particular valve replacement procedure. Thus, for example, sections of the valve assembly may be assembled at a remote site, such as, for example, in the ascending aorta or descending aorta, and then delivered to the target site, where the valve assembly is then connected to the support structure. Alternatively, the valve assembly may be combined with the support structure at a remote site and then the assembled valve device may be delivered to the target site. As a further alternative, the valve device may be entirely assembled at the target site.

A valve module may be affixed to the support structure and/or valve sections may be attached to each other with locking mechanisms. The locking mechanisms of the present invention may be integral to the device modules, meaning that the locking mechanisms are, in their entirety, part of the structure of the device modules or attached to one or more device modules prior to delivery and deployment into a body lumen. Alternatively, the locking mechanisms of the present invention may be non-integral to the device modules, meaning that at least part of the locking mechanism is a structure apart from the modular valve device, i.e., it is applied to one or more device module after delivery and deployment of the device module(s) into the body, or removed from the valve device in the process of locking or after locking.

For example, in one embodiment, the valve module may contain a set of lockable tabs that, when engaged, exert sufficient radial force upon the support structure to bind it to the valve module. In another embodiment, the support structure may contain a set of geometrical engagement structures, for example a ring in a groove, that engage a portion of the valve module designed to exert outward radial force against the support structure. In yet another embodiment, the valve module and support structure may each have female components, and a locking tab having male components may be inserted into the assembled valve device and placed in a manner to mate with both the valve module and support structure of the assembled valve device to hold the two components together. In still another embodiment, a set of pins or rivets may join the valve module to the support structure. In a further embodiment, the edges of an unassembled valve module may include interlocking geometries, that permit a zip-lock-type attachment to lock the edges together. Several other embodiments of locking mechanisms are within the scope of the invention, as described herein or as readily discernable to the skilled person. The integral locking mechanisms may allow the portions of the device modules that are to be locked together to self-engage once properly positioned.

Device modules may also be fixed in place by friction or other positive location forces such as magnetic forces, interference fit or tight fit. Pull wires or push-rods may be used to position the valve sections relative to one another during assembly of the valve sections to form the valve assembly, and may also be used to assist in positioning the valve module (e.g., the valve assembly) within the support structure when combining the device modules to form the assembled valve device. Pull wires may also serve to tether device modules during delivery, so that the modules may be delivered and deployed in tandem.

Also provided is a system for valve delivery that permits valve function to be maintained while the modular valve device is assembled and placed at the site of implantation, and a method of maintaining valve function while assembling and implanting a percutaneous modular valve device with precision, by providing a temporary valve. In one embodiment, the temporary valve may be part of the delivery system (e.g., attached to the delivery device) and may be removed when the delivery system is extracted from the vessel. In another embodiment, the temporary valve may be mounted on the support structure of the permanent valve device, and implantation of the valve module of the permanent valve (e.g., leaflets substructure, valve assembly or individual valve sections) may crush or flatten the temporary valve leaflets. The method of delivering a modular prosthetic valve may include an intermediary step of deploying a temporary valve. While not required for the method of delivering a modular valve device, use of the temporary valve in accordance with the invention is intended to improve the safety and outcomes of percutaneous valve replacement procedures.

Advantages that may be achieved by the present invention include that the percutaneous prosthetic valve system according to the invention reduces the bulkiness of the valve for delivery and increases the flexibility of the delivery device. Also, the prosthetic valve device is minimally invasive and the method of percutaneous delivery reduces traumatic damage and minimizes procedure complications, thereby increasing the safety of the procedure and expanding the number of medical facilities equipped to perform percutaneous valve replacement procedures. An advantage of installing a temporary valve before implanting the permanent prosthetic valve is that it alleviates the time pressure for assembly and placement of a percutaneous valve device by preventing wide open regurgitation during the replacement procedure. The use of a temporary valve provides the operator with some leeway time to assemble the modular percutaneous valve device, to position the prosthetic valve device with care and precision, and to adjust the position of the valve without adversely affecting the outcome of the valve replacement procedure.

BRIEF DESCRIPTION OF THE DRAWINGS

FIGS. 4A-C illustrate an embodiment of how pull wires may be used to assemble an embodiment of a valve device comprising four device modules. FIG. 4A depicts pull wires threaded through unassembled modules of a valve device such as the embodiment depicted in FIG. 3. FIG. 4B depicts the use of a pull wire and a push-rod to assemble valve sections into a valve assembly. FIG. 4C depicts the use of a pull wire and a push-rod to assemble a valve assembly and support structure into a valve device.

FIGS. 7 and 7A illustrate an embodiment of a locking mechanism for attaching the valve leaflets of FIG. 2 to one another to form the valve assembly.

FIGS. 8A-C illustrate an embodiment of a locking mechanism for attaching the valve module onto a support structure.

FIGS. 10A-D illustrates an embodiment of a stud-and-harbor lock as an integral locking mechanism for attaching a valve module to a support structure. FIG. 10A depicts the studs located on a ring of the valve module and the harbor located on a post of the support structure; FIG. 10B depicts a stud docking in a harbor located on a post of the support structure; FIGS. 10C and 10C' depict a vertical channel on the stud, as part of ridge and channel-based lock between the stud and harbor, in a front and top view, respectively; FIGS. 10D and 10D' depict a vertical ridge on the harbor, as part of a ridge and channel-based lock between the stud and the harbor, in a side and front view, respectively.

FIGS. 12A-B illustrate an embodiment of a snap fit lock as an integral locking mechanism and as a non-integral locking mechanism. FIG. 12A depicts a non-integral snap-fit lock for attaching the valve module to the support structure; FIG. 12A' illustrates the snap-fit prong; FIG. 12B shows another embodiment of the non-integral snap-fit lock with a snap-fit receptacle attaching the valve module to the support structure.

FIGS. 13A-E illustrate interlocking geometries as non-integral locking mechanisms for attaching the valve module to the support structure. FIG. 13A depicts a pin; FIG. 13B illustrates a pin in use; FIG. 13C illustrates a peg; FIG. 13D illustrates a rivet; FIG. 13E illustrates a stud-and-tube connector.

FIG. 14A illustrates how the sides of an unassembled valve module may be attached with the interlocking curvilinear groove mechanism, from a lateral view, using strings; FIG. 14B illustrates the cross-section of an embodiment of the interlocking curvilinear groove mechanism; FIGS. 14C and 14C' illustrate the cross-section of another embodiment of the interlocking curvilinear groove mechanism, unlocked (FIG. 14C) and locked (14C').

DETAILED DESCRIPTION OF THE INVENTION

Figure 1:
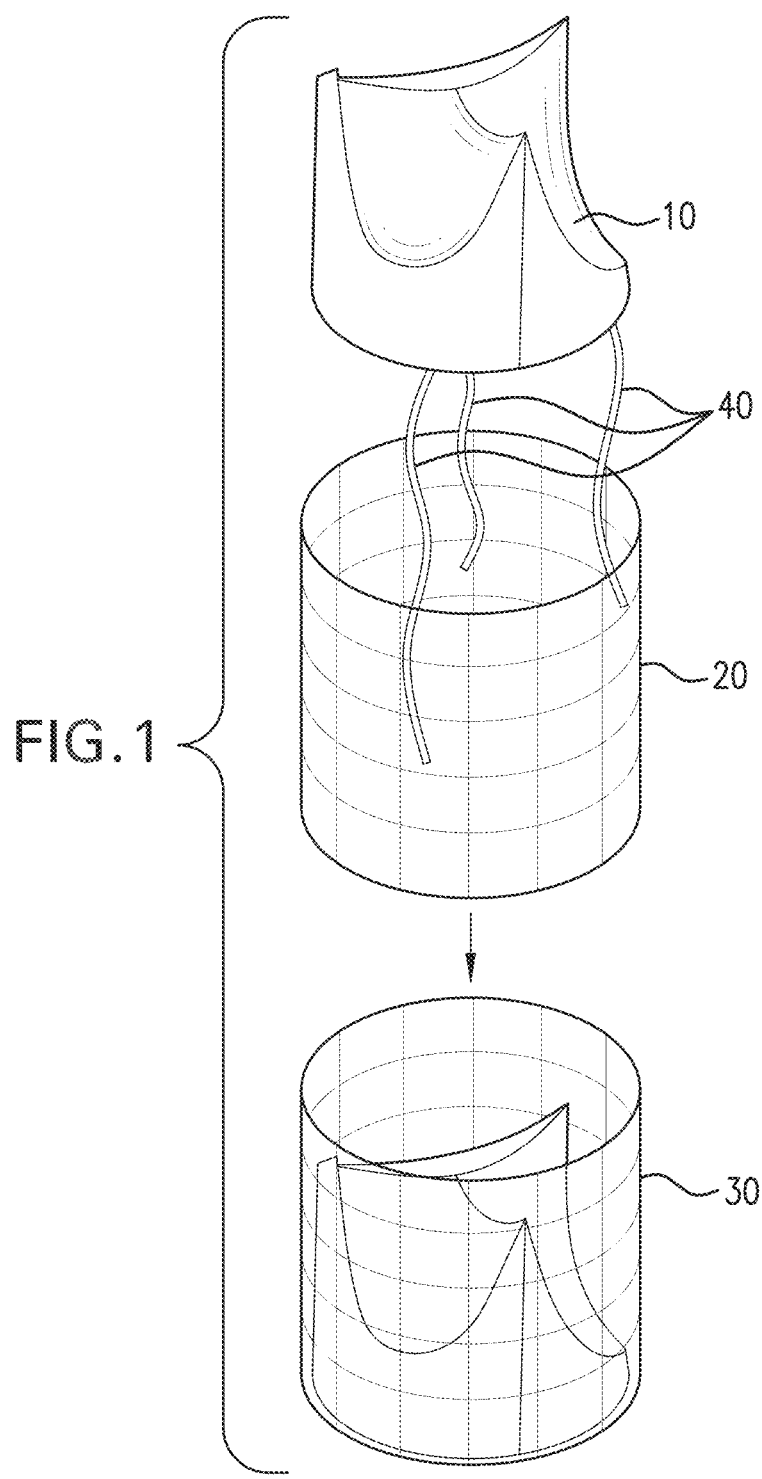
FIG. 1 illustrates an embodiment of assembling a modular prosthetic valve device (bottom) by combining a valve module (shown at the top) and a support structure (center), in this embodiment using pull wires.

The present invention provides implantable modular percutaneous prosthetic valve devices, systems and methods for percutaneously delivering and deploying implantable percutaneous modular heart valve devices and other implantable percutaneous modular valve devices in body lumens. The invention provides a modular prosthetic valve system that allows a prosthetic valve device to be delivered safely into a lumen without the need for invasive surgery.

The artificial valve device of the invention comprises a plurality of device modules for delivery and assembly in vivo. The device modules may be delivered to a desired location in the body, for example near the site of valve implantation, at the site of valve implantation, or at a location some distance from the site of implantation, where they may be assembled to form the assembled valve device. From a functional perspective, the plurality of device modules may include a support structure and a valve module. The support structure provides the framework, or backbone, of the device, housing the valve module and holding the valve module in place within the body lumen. The valve module comprises the leaflets of the valve device and when assembled into a working configuration provides a conduit having a inlet end and an outlet end. The valve module may comprise a plurality of device modules or it may be one device module.

As used herein, the term "device module" refers to components of the modular valve device, e.g., a support structure, a leaflets substructure, or a valve section (e.g., part of a valve assembly), that are delivered unassembled and then may be assembled into the valve device in vivo. As used herein, the term "valve module" refers to the one or more device modules that may be delivered in an unassembled, folded configuration and assembled to form the portion of the permanent valve device comprising one or more leaflets, such as a valve assembly. Thus, the valve module itself may comprise one or more device modules. The term "temporary valve" refers to the valve that is installed for temporary functioning, as distinguished from the modular valve device, which is the "permanently" installed valve. The terms multi-component and modular are used interchangeably herein. The terms "site of implantation," "location of implantation," and "target site" are used interchangeably herein.

In one embodiment, the modular valve device comprises a plurality of device modules: a support structure and a plurality of valve sections (each comprising a valve leaflet) that may be assembled into a valve assembly. The plurality of valve sections are shaped such that they can fit together to form the valve assembly, which opens and closes to permit one-way fluid flow. The valve sections or leaflets function in a manner that closely matches the physiological action of a normally functioning native valve. The support structure and valve sections may be delivered into the lumen sequentially. Valve sections may be combined into a valve assembly within the support structure, or they may be combined into a valve assembly which is then combined within the support structure. Alternatively, valve sections may be attached to the support structure one-by-one to form the assembled valve device.

In another embodiment, the modular valve device may comprise a plurality of valve sections that are delivered, assembled and implanted without a support structure.

The valve assembly—which may have, but is not limited to, a three leaflet arrangement—may be mounted on a support structure adapted to be positioned at a target location within the body lumen. The valve assembly may comprise 2, 3, 4 or more valve sections. The support structure may be adjustably connected to the vessel wall and the valve module may be adjustably connected to the support structure in an way that allows fine readjustment of position of the support structure relative to the vessel wall or of the valve module relative to the support structure after deployment.

In yet another embodiment, the modular valve device comprises two device modules, a support structure and a valve module that is a single-piece valve component, which two device modules may be delivered to the lumen sequentially and assembled in the body. The single-piece valve component may have an unassembled configuration, which provides a useful shape for folding the valve component into a low profile delivery configuration, and an assembled working configuration having a conduit.

In one embodiment, the one-piece valve component may be, in an unassembled configuration, a leaflets substructure—a substantially flat, one-layer structure having a first end, a second end, and a base-to-apex axis. The unassembled leaflets substructure may be rolled into a delivery configuration, for example by rolling along a single axis, delivered apart from the support structure (or fixedly connected to the support structure), unrolled and assembled to a valve component (working configuration), and the first and second ends may be locked together. The leaflets substructure includes a plastically deformable member that may be rolled with the leaflets substructure and formed into a ring to assist in transforming the leaflets substructure into its assembled working configuration. In another embodiment, the one-piece valve component may be, in an unassembled configuration, a leaflets-ring—a substantially flat, two-layer structure having a first end, a second end, and a base-to-apex axis. The unassembled leaflets-ring may be rolled into a delivery configuration, for example by rolling along single axis. The folded, unassembled leaflets ring may be delivered, and then unfolded and assembled to a valve component (working configuration). The leaflets-ring includes a plastically deformable ring member having an unassembled configuration that may maintain the leaflets-ring in its unassembled configuration and an assembled configuration to which it may be expanded to maintain the leaflets-ring in its assembled, working configuration.

In either embodiment, after transforming the unassembled shape into an assembled working configuration, the one-piece valve component may then be combined with and locked onto the support structure to form the assembled valve device. Examples of similar single-piece valve components comprising self-assembly members and how they may be folded and assembled using a self assembly member, are described in detail in FIGS. 2a-4b and ¶¶43, 48-57 of co-pending U.S. patent application Ser. No. 12/686,338 (self-assembly), entitled "Self-Assembling Modular Percutaneous Valve and Methods of Folding, Assembly and Delivery," filed on date even herewith, which is incorporated herein by reference.

In still yet another embodiment of the modular valve device, the support structure may be provided as more than one device module. For example, the support structure may be divided along the circumferential axis to comprise, for example, two expandable tubular structures that may be aligned longitudinally and assembled by linking them together. In such an embodiment, each portion of the multi-part support structure could have greater radial rigidity than a single piece support structure, yet retain longitudinal flexibility during delivery by being delivered as more than a single compressed tube. Alternatively, the support structure may be divided along a longitudinal axis, and delivered as two halves of a tube, each half capable of being compressed to a diameter smaller than a whole support structure.

As used herein, "assembled" means that the valve assembly, valve component, or valve device is in a working configuration (e.g., substantially tubular, rather than flat, rolled or separate device modules), but the modules are not necessarily locked together. The assembled configuration may also be referred to as a working configuration, in which the valve module is substantially tubular and provides a conduit with the leaflets in place. The "unassembled" valve module may be folded for delivery (a delivery configuration) or unfolded and ready for assembly. The "unassembled" single-piece valve component may include a leaflets substructure, having first and second ends, which as set forth above may be arranged into a ring so that the ends meet to form the assembled valve component (working configuration). Similarly, as set forth above, the valve assembly "unassembled" includes a plurality of valve sections, which may be attached to one another in tandem, e.g., laid out in a series rather than arranged in a ring, to optimize folding of the modules for delivery. Alternatively, the valve sections may be unattached and delivered separately.

The unassembled configuration of the one or more device modules that make up a valve module provides a particular advantage for delivery, because valve module may be folded to a delivery configuration that minimizes the diameter of the valve module for delivery, a feature not available in current percutaneous valve devices.

The present invention provides locking mechanisms for attaching together modules of an implantable modular percutaneous valve device or ends of a single piece unassembled valve component. The locking mechanisms of the invention may be integral locking mechanisms or non-integral locking mechanisms. By "integral," it is meant that the component(s) of the locking mechanism are contiguous with one or more device modules, in that they are attached to or structurally part of the device modules during delivery. The integrated locking mechanisms generally effect locking of the device modules during or after assembly. By "non-integral," it is meant that the locking mechanism comprises one or more structures separate and apart from the device modules, preferably delivered in the same delivery device as the device modules, and applied to the device modules after the valve device is assembled to lock them together or removed from the valve device in the process of locking or after locking. For example, the non-integral locking mechanisms may be delivered separately and applied to device modules after the valve device is assembled to lock them together. Alternatively, the non-integral mechanism may be a member that prevents locking, such as a blocking tab, that may be removed to permit the modules to lock together. The non-integral locking mechanisms may in part use integral features of the device modules, for example holes, grooves or other structural parts, to which the non-integral part interacts. The integral locking mechanisms of the invention also may be applicable to locking together parts of a pre-assembled percutaneous valve device.

For example, the valve sections (or sides of a leaflets substructure) may be attached by integral locking mechanisms, such as male-female coupling type components; slotted hook mechanisms; interlocking curvilinear groove (zip-lock) mechanism; interference-fit; friction locking; an integral snap-fit mechanism comprising a snap-fit prong and snap-fit receptacle; as well as hook-and-eye components; fish-hook; interconnecting or interlocking geometries (e.g., dovetail or pins, pegs, rivets or stud-and-tube connectors. Alternatively, valve sections or sides of a leafets substructure may be attached together using separate (non-integral) locking components, such as a non-integral snap-fit mechanism comprising a snap-fit prong and snap-fit receptacle; press-fix connectors; and non-integral interlocking geometries, such as pins, pegs, rivets and stud-and-tube connectors.

Similarly, the present invention provides locking mechanisms for attaching the valve module and support structure to one another. For example, the valve module and support structure may be attached with integral locking mechanisms, such as: hook-and-groove components; slotted hook mechanisms; a locking tab; stud-and-harbor lock; male-female coupling components; integral snap-fit mechanism; hook-and-eye components; fish-hook; and integral interlocking geometries such as pins, pegs, rivets, and stud-and-tube connectors. Alternatively, the valve module and support structure may be attached together using separate (non-integral) locking components, such as: press-fix connectors; non-integral snap-fit mechanisms; and non-integral interlocking geometries, such as pins, pegs, rivets, and stud-and-tube connectors.

The locking mechanisms may be manufactured from the same materials as the support structure, for example, stainless steel, shape memory alloy, such as, for example, nitinol, or an amorphous metal of suitable atomic composition, for example, cobalt chromium, or fashioned from the valve module material, or from other suitable biocompatible materials as would be recognized in the art.

The system of the invention comprises the modules of the valve device and a delivery device. The modular valve device is delivered in parts in the delivery device. The two or more modules of the valve device may be provided pre-loaded in a delivery device such as catheter or other similar device known in the art, or may be loaded into the delivery device after the delivery device is inserted into the body lumen. The support structure and valve module (or valve sections) may be loaded in tandem into the catheter. Alternatively, the support structure may be loaded into the catheter first and delivered, then the valve module or valve sections may be loaded in tandem into the catheter and delivered into the support structure where the complete device is assembled.

The present invention also provides methods for delivering a modular valve device to a target location in a lumen and assembling a modular valve device. The device modules may be serially delivered within an appropriate delivery device such as a catheter, for example an endovascular catheter or an endolumenal catheter. The device modules may be provided pre-loaded in the delivery device, or may be loaded into the delivery device after the delivery device is inserted into the body lumen. The device modules may be delivered in any order. In a particular embodiment, where the device modules include a support structure and a plurality of valve sections, the support structure may be delivered first, followed by each of the valve sections.

After delivery and deployment from the delivery device, the device modules may be assembled in the body, for example in a body lumen—such as in the body lumen or at the site of implantation, to form a fully assembled valve device, and attached together using the locking mechanisms of the invention. The device modules may be assembled using, for example, pull wires for positioning the modules or portions of the modules relative to one another. For example, a plurality of valve sections may be connected via pull wires for sequential delivery, and then after being delivered in tandem and positioned at the target site, the pull wires may be used to position the device modules relative to one another during assembly of the valve sections. The pull wires may also facilitate the connection of the valve sections to the support structure via the locking mechanisms and assist in positioning the valve assembly within the support structure to form the assembled valve device. In other embodiments, push-rods may be used alone or with other members, for example, in conjunction with pull wires, to assemble the device modules. Push-rods may be, for example, stiff wires or tubular structures. Remote manipulation of the device modules facilitates assembly of the parts within the body. Alternatively, the device modules may be assembled at least in part using a self assembly member, e.g., a shape memory wire or band, as described in detail in ¶¶38-38, 45-46, 51-69 and FIGS. 2a-10 of co-pending U.S. application Ser. No. 12/686,338 (self-assembly), filed on date even herewith, which application is incorporated herein by reference. For example, a leaflets substructure may be delivered attached to a self-assembly member, which—with or without the use of push-rods—is used to assemble leaflets substructure into a valve component, the edges of the leaflets substructure being brought together, wherein a locking mechanism in accordance with the present invention may lock the edges of the leaflets substructure together. A second self-assembly member may assist in the assembly of the valve component and the support structure, which may then be attached using a locking mechanism of the present invention. The valve module may be connected to the support structure in an adjustable manner that will allow final adjustments of position of the valve module after implantation of the valve device. Non-integral locking mechanisms similarly may be delivered and deployed via the delivery device.

The methods described herein enable percutaneous delivery of a prosthetic artificial valve through a smaller diameter lumen than currently required for percutaneous artificial valves in the art by delivering the valve device as unassembled sections and assembling the valve sections in the body. By assembling the modules of the valve device piece by piece, for example, at the final location of implantation or within the body lumen, e.g., ascending aorta, before relocation of position to the final target site, the size of the orifice necessary for entry into the body of the prosthetic valve is reduced and the ease and flexibility of delivery of the device to the desired location in the vessel is increased. The reduced profile of the unassembled valve device of the invention permits the delivery device of the invention to have a significantly smaller diameter compared to the typical diameter of delivery devices required in the art. Thus, for example, a delivery device in the present invention may have a diameter lower than 15 french, or 5 mm.

The system of the invention may further include a device for maintaining valve activity while assembling and implanting a modular valve device. For example, to allow assembly of the percutaneous modular valve to proceed for a period longer than about 30 seconds, a temporary valve that will function during assembly and implantation of the modular valve device may be used to maintain valve activity. Because it is used only temporarily, a temporary valve need not function optimally, repeatedly and predictably over extended periods of time, as a permanent valve must. It also need not open fully or close fully. Because a temporary valve does not need to have the same precision and duration of function, be made of the same materials or have the same long-term viability in the body, a temporary valve can have a more efficient design. It can be made of a thin material, and the leaflets need only be partially attached to have sufficient temporary function during the replacement procedure, and therefore the temporary valve can be constructed to take up less space, for example during delivery.

In one embodiment, the temporary valve may be mounted on the delivery device and deployed quickly without need for precise placement to maintain valve function while the modular valve device is assembled and accurately placed at the location of implantation. The temporary valve may be placed at the site of permanent valve implantation or at a position removed from the site of permanent valve implantation. In another embodiment, the temporary valve may be attached to the support structure to establish some valve function as soon as the support structure is expanded and implanted. This gives the operator time to assemble the valve module(s) and move it into position in the support structure with precision and less concern over interruption in proper blood flow. The valve module(s) may be placed over the temporary valve and combined with the support structure. Preferably, the temporary valve is a single piece structure, for example a membrane with a simple design that is easy to fold for percutaneous delivery, easy to install, and easy to pop open for operation. Alternatively the temporary valve may comprise more than one piece, but preferably still is easy to fold for delivery, easy to install and easy to pop open for operation.

When the temporary valve is delivered folded inside the compressed support structure, a smaller delivery profile may be achieved than can be achieved with a permanent pre-assembled percutaneous valve device, because the temporary valve may have a simpler geometry and may be manufactured from thinner, less durable materials than the permanent valve module. In some aspects of this embodiment, the temporary valve may be constructed of biodegradable material.

The devices, systems and methods of the invention are particularly adapted for use in percutaneous aortic valve replacement, but may also find use as replacements for other cardiac valves, such as, e.g., pulmonic, mitral and tricuspid valves, as well as valves in the peripheral vasculature or in other bodily lumens, such as the alimentary canal, lymph ducts, the biliary duct, and any other lumens having valves requiring replacement or needing valve implantation. Where the modular valve device is designed to replace an aortic valve, it may be assembled in the ascending aorta, the descending aorta, in the ventricle, at the implantation site, or part at the implantation site and part in the aorta. Although particularly adapted for use in lumens of the human body, the devices, systems and methods may also find application in animals.

The valve component and valve assembly of the modular valve device may be manufactured from suitable materials, such as polymers, metals or biological material. The selection of material, structure and method of manufacturing preferably is made to optimize the function, the durability and the biocompatibility of the valve.

The support structure preferably is expandable, so that it may be delivered compressed (unexpanded), and then expanded for implantation and assembly of the valve device. The support structure may be manufactured from a biocompatible material that is sufficiently durable that the structure can support the valve component while maintaining the device's position in the lumen. The support structure material also is compatible with delivery of the support structure in a compressed state and expansion of the compressed support structure upon deployment in the lumen. In one embodiment of the present invention the support structure is manufactured from stainless steel or a shape memory alloy, such as, for example, Nitinol. In another embodiment, it may be made of an amorphous metal alloy of suitable atomic composition, as are known in the art. Other further embodiments may be manufactured from similar biocompatible materials known in the art. In one embodiment, the support structure is annular, but it may be provided in other shapes too, depending on the cross-sectional shape of the lumen at the location the valve is to be implanted. One non-limiting example of an appropriate support structure is a stent. The stent, or any other support structure, can be self-expanding or balloon-expandable. Other similar support structures are known in the art and are interchangeable with a stent in accordance with the invention.

When deployed, the support structure should engage the lumen wall so as to be secure therein so that the valve assembly does not shift in the lumen and is not displaced from the desired location, for example from the pressure of fluid flow through the valve or its impact on the closed valve. The support structure may include locking mechanisms, such as those described herein, to secure the valve assembly (or valve component) within it. The support structure may further include hooks, ribs, loops or other anchoring devices to facilitate the anchoring of the assembled valve device to the lumen wall. The connection of the support structure to the vessel wall and of the valve assembly to the supporting structure may be adjustable in position.

The devices and methods of the invention are particularly adapted for use in percutaneous aortic valve replacement, but may also find use as replacements for other cardiac valves, such as, e.g., pulmonic, mitral, and tricuspid valves, as well as valves in the peripheral vasculature or in other bodily lumens, such as the alimentary canal, lymph ducts, the biliary duct, and any other lumens having valves requiring replacement or needing valve implantation. Where the modular valve device is designed to replace an aortic valve, it may be assembled in the ascending aorta, the descending aorta, the left ventricle, at the implantation site, or part at the implantation site and part in the aorta. Although particularly adapted for use in lumens of the human body, the devices, systems, and methods may also find application in animals.

The aforementioned embodiments as well as other embodiments, delivery methods, different designs and different types of valve devices and locking mechanisms are discussed and explained below with reference to the accompanying drawings. Note that the drawings are provided as an exemplary understanding of the present invention and to schematically illustrate particular embodiments of the present invention. The skilled artisan will readily recognize other similar examples equally within the scope of the invention. The drawings are not intended to limit the scope of the present invention as defined in the appended claims.

FIG. 1 illustrates one embodiment of how the valve module 10 and support structure 20 of a modular artificial valve device may be assembled. For purposes of showing how the valve module and support structure are combined to form the assembled valve device, in FIG. 1 the valve module is shown assembled, and may represent a valve assembly or valve component. In this embodiment the valve module 10 and a support structure 20 may be assembled with pull wires 40 or the like, resulting in an assembled valve device 30. The support structure 20 and the valve module 10 may be delivered sequentially, optionally in tandem, as depicted in FIG. 1—in which case the modules may be tethered by pull wires 40. The valve module 10 may be pulled into the support structure 20 using the pull wires 40, which may be connected to both modules, and then the valve module 10 may be attached to the support structure 20. This assembling step may be carried out, for example, in the lumen of the aortic outflow tract or in the ascending aorta. Attachment of the valve module 10 to the support structure 20 may be by any of several locking mechanisms, as described herein. Alternatively, the support structure 20 and valve module 10 may be delivered separately, i.e., not in tandem (not shown). For example, the support structure 20 may be delivered and deployed at the final location and then the valve module 10 delivered and deployed within the support structure 20 thereby assembling the modules into the assembled valve device 30.

Figure 2:
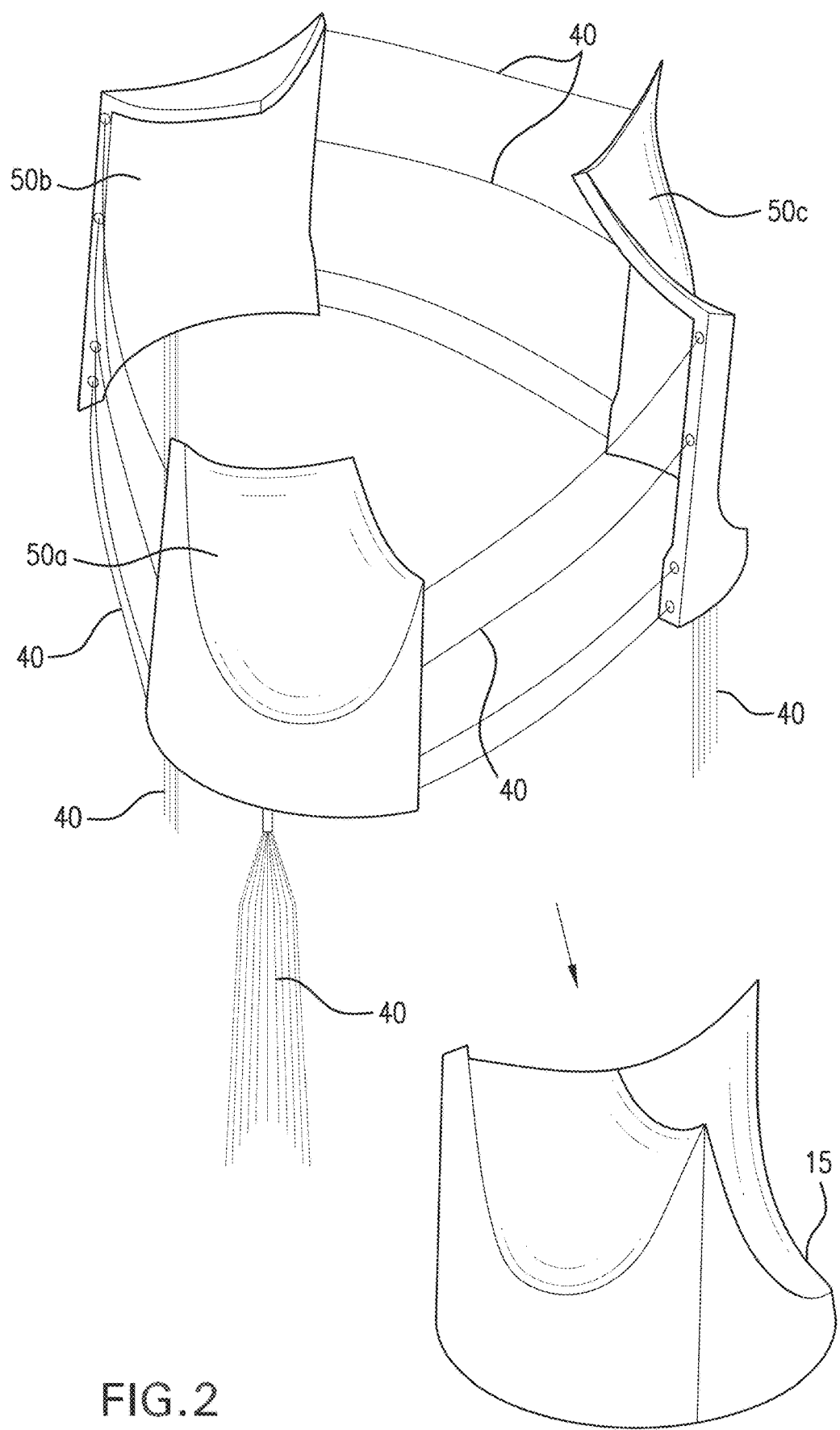
FIG. 2 illustrates an embodiment of a valve module that comprises a plurality of valve sections. In this example, three valve sections are assembled to form a valve assembly.

FIG. 2 illustrates an embodiment of the modular valve device having four device modules: a support structure (not shown) and three valve sections 50a-50c. The valve sections 50a-50c are designed to fit together to form a valve assembly 15. In use, the valve sections operate much as the folds of tissue in a native valve. The valve sections 50a-50c may be pre-fitted with and tethered by pull wires 40 or strings.

The pull wires 40 or strings may have a dual purpose. First, the pull wires 40 may tether the valve sections 50a-50c together for delivery purposes, so that they may be delivered through the lumen in tandem. Second, the pull wires 40, which extend out the end of the catheter, may be pulled to assemble the valve sections 50a-50c to yield the valve assembly 15. As an example of how the pull wires may be used to assemble the modular valve device of FIG. 2, the pull wires may be tightened one by one to pull the valve sections together to form the valve assembly within the support structure, or alternatively to pull the valve sections together outside the support structure to form the completed valve assembly and then to guide the valve assembly into the support structure. Other means for positioning and attaching valve sections may be used and are readily discernible to the skilled person in view of the disclosure herein.

In one aspect of this embodiment (not shown), pull wires may also connect the valve sections 50a-50c to the support structure 20 (see FIG. 3) such that the pull wires 40 may be pulled to assemble the valve assembly 15 and support structure 20, in a manner similar to that depicted in FIG. 1, to yield the assembled valve device (not shown). The exact number of valve sections may differ from one embodiment to the next, in particular a valve assembly may include, for example, from 2-6 valve sections or more. In one embodiment, an assembled valve device designed to replace a tricuspid valve may have four device modules: three valve sections that form an assembled valve assembly, which is secured within the lumen by a support structure. An assembled valve device designed to replace a mitral valve may have, for example, three device modules: two valve sections that form an assembled valve assembly that is secured within the lumen by a support structure.

Figure 3:
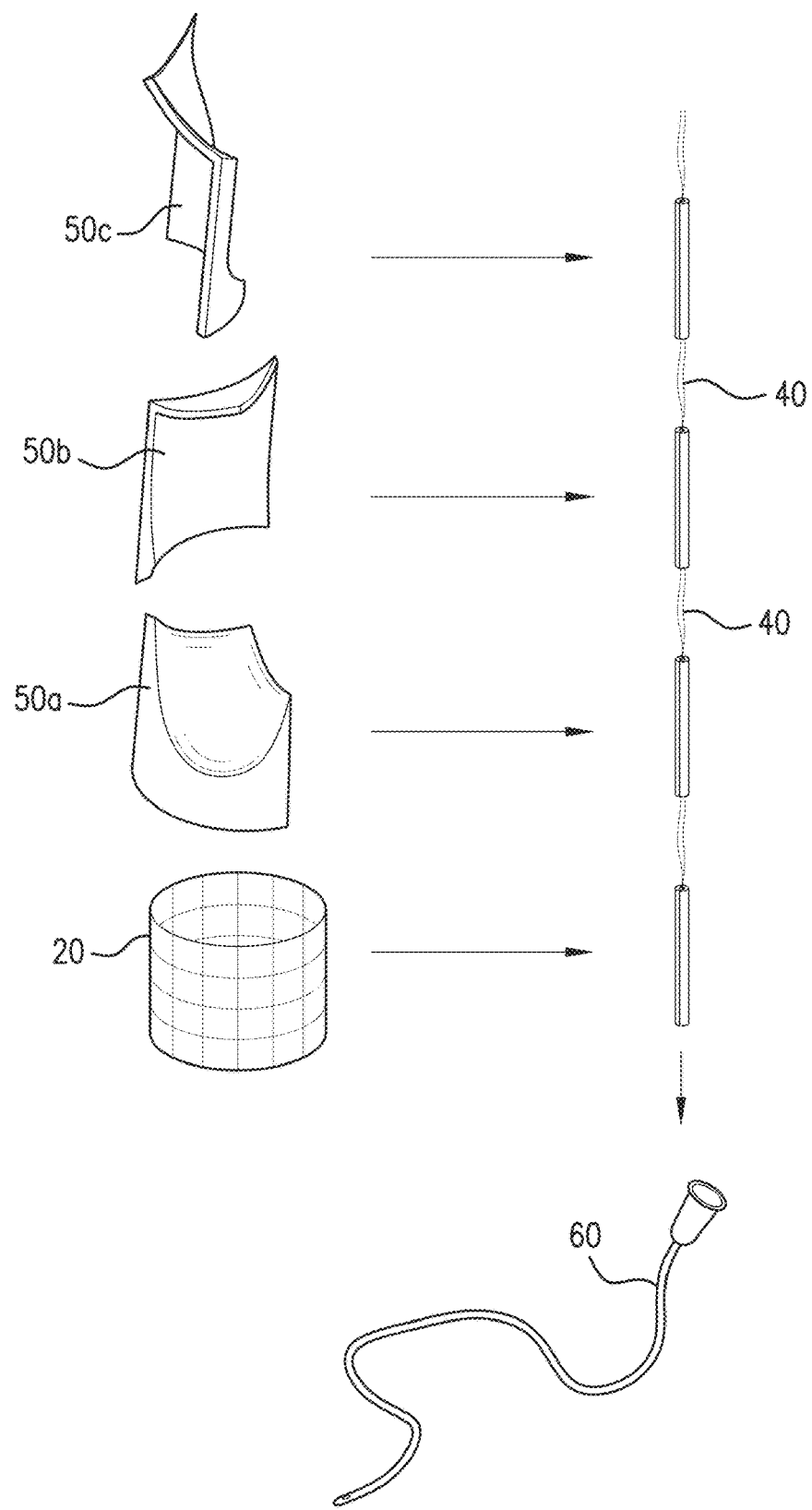
FIG. 3 illustrates a valve device comprising four device modules: three valve sections (making up the valve module) and a support structure, which may be loaded in series onto a delivery device—in this embodiment a catheter, wherein the catheter provides a vehicle for delivery and deployment of the device modules to a desired site in the body.

FIG. 3 schematically illustrates how the four modules of the embodiment depicted in FIG. 2 may be packaged for delivery into a body lumen. The four device modules may be tethered by pull wires and delivered in tandem, with the support structure as the lead device module, as illustrated. Alternatively, the valve sections may be delivered in tandem, but the support structure untethered to the valve sections. As shown in FIG. 3, the support structure 20 and three valve sections 50a-50c are loosely connected by pull wires 40 in a manner that permits sequential delivery and assembly. As illustrated on the right side of the figure, the modules are folded into a delivery configuration for loading into the delivery device, in this case a catheter 60. The support structure 20 may be self-expanding, and/or it may be crimped on a balloon for delivery and deployment, or it may be expanded from its compressed configuration by other means known in the art. The train of modules (in FIG. 3 there are four) is then introduced into the catheter 60; the loaded catheter is then ready to be used to deliver the modules to the site of deployment in the lumen. The valve device modules may be put into the delivery device before it is inserted into the lumen or after it is inserted into the lumen, depending on the demands of the particular procedure. In an embodiment in which the catheter 60 is an endovascular catheter, it may be capable of being mounted on a guide wire.

The method of delivering and assembling an embodiment of the modular prosthetic valve device of the invention comprising the valve assembly 15 of FIG. 2 may, for example, proceed as follows: a delivery device, such as a catheter 60, carrying a support structure 20 and multiple valve sections 50a-50c, as illustrated in FIG. 3, may be fed through the appropriate vessels to the final location where the valve device is to be implanted. The support structure may be deployed first so as to be capable of receiving the valve sections. Once the support structure is in place, the valve sections 50*a*-50*c* may be deployed sequentially; in the embodiment illustrated in FIG. 3, the valve sections are tethered together and deployed in tandem. The valve sections 50*a*-50*c* may be combined, for example using the pull wires 40, to yield the valve assembly 15, as described above. The modules of the valve assembly 15 may be assembled within the support structure 20 or they may be assembled outside the support structure 20 and then the valve assembly 15 may be positioned in the support structure 20 as described for FIG. 1. When the valve sections 50*a*-50*c* are assembled to form a valve assembly 15 within the support structure 20, each valve section 50*a*-50*c* may be sequentially attached to the support structure 20 and then attached to one another. The valve sections 50*a*-50*c* may be attached to one another, and the valve assembly may then be secured to the support structure, by any of several locking mechanisms, as described herein. The valve device of FIGS. 2 and 3 may be assembled in the body and then positioned for implantation at the final location or it may be assembled at the final location. Optionally, additional anchoring mechanisms may be adapted and used to guide and/or secure the completely assembled valve device to the lumen walls or remnant tissue of the native valve wall.

Pull wires may be threaded through the valve assembly and support structure in a manner that loosely tethers them for delivery but also in a manner that permits the modules of the device to be combined or assembled when the pull wires are pulled by an operator. The pull wires may be tethered to the modules of the modular prosthetic valve device by any appropriate means known in the art, which tethering is reversible by pulling on one end of the wire for removal of the pull wires after the device is implanted and secured to the body lumen. Thus, for example, the modules of the valve device may comprise loops or small holes through which the pull wires are threaded. Alternatively the pull wires may be integral to the delivery system which includes mechanisms for manipulating the pull wires to assemble the valve sections and combine the valve assembly and support structure. For example, an activator in the delivery system a mechanical mechanism or an electrical current may be used to pull the pull wires to assemble the device modules.

Figure 4A:
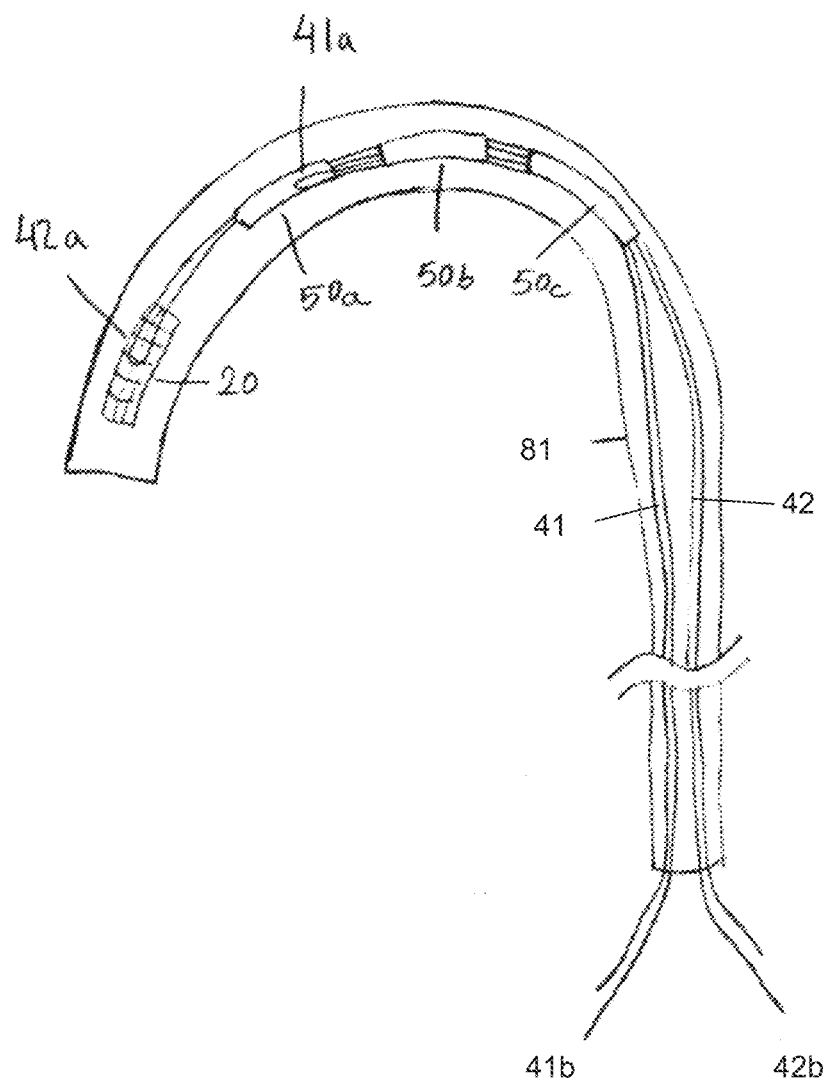

FIGS. 4A-4C provide one example of how device modules may be assembled using pull wires and push-rods. Other methods for positioning and assembling the device modules of the invention may also be used with the invention, for example pull wires alone, push-rods alone or in conjunction with self-assembly member, and self-assembly members alone, for example shape-memory wires. Self-assembly members are described in detail in ¶¶36-38, 45-46, 51-69 and FIGS. 2A-10 of co-pending U.S. application Ser. No. 12/686,338 (self-assembly), filed on date even herewith, which application is incorporated herein by reference.

In particular, FIGS. 4A-4C illustrate one way pull wires and push-rods having a tubular structure may be used to assemble an embodiment of the modular valve device comprising four modules, such as the embodiment illustrated in FIG. 3. FIG. 4A depicts a first pull wire 41 threaded through valve sections 50*a*-50*c* and comprising a first loop 41*a*, and a second pull wire 42 threaded through the valve sections 50*a*-50*c* and a support structure 20 and comprising a second loop 42*a*, disposed in a body lumen, such as an aorta 81. For clarity of illustration, the delivery device is not drawn in any of FIGS. 4A-4C. The first loop 41*a* may be laced through the first valve section 50*a* and the ends 41*b* of the first pull wire 41 may extend out the proximal end of the delivery device. The first pull wire also may be laced through the other valve sections (not shown, for clarity of illustration). The second loop 42*a* may be laced through the support structure 20 and the ends 42*b* of the second pull wire 42 may extend out the proximal end of the delivery device.

FIG. 4B illustrates a later stage of assembly, where the valve sections have been assembled into the valve assembly 15 using the first pull wire 41 in the aorta 81. In this embodiment two push-rods having tubular structures are used with the pull wires 41 for assembling the device modules, and are referred to in FIGS. 4B and 4C as a first tube 63 and a second tube 64, however one or more structures may be used as a first tube 63 and a second tube 64. To assemble the valve sections 50*a*-50*c* as shown in FIG. 4A), a first tube 63 may be placed over the ends of the pull wire 41, inserted into and through the delivery device, and advanced to the most proximal valve section (e.g., 50*c* in FIG. 4A) in the aorta 81. Then, both ends 41*b* of the first pull wire 41 may be pulled relative to the first tube 63 to assemble valve sections together to form the valve assembly 15, as shown in FIG. 4B, and to assist in locking the valve sections together. The first tube 63 may then be removed. FIG. 4B shows that in this embodiment the first loop 41*a* ends up laced through the circumference of the valve assembly 15, however the first pull wire 41 and first loop 41*a* may be laced through the valve sections in any manner that facilitates assembly of the valve sections into a valve assembly. The first pull wire 41 may be removed by pulling on one end. Alternatively, the first pull wire 41 may be tied off and then cut, leaving the valve assembly connected. The second loop 42*a* remains laced through the still separate support structure 20 and the second pull wire 42 remains threaded through the valve assembly 15.

The support structure 20 may then be positioned at the target point of implantation 70 of the valve device and expanded. As depicted in FIG. 4C, to assemble the support structure and valve device, a second tube 64 may then be placed over the ends of the second pull wire 42, inserted into and through the delivery device (not shown), and advanced to the valve assembly 15. Then, both ends 42*b* of the second pull wire 42 may be pulled relative to the second tube 64 to assemble the valve assembly 15 and support structure 20 into an assembled valve device. Specifically, the second pull wires 42 may be used to properly position the valve assembly 15 relative to the support structure 20. The position of the valve assembly 15 may be adjusted by a graded pulling of the second pull wire 42 and then locked to the support structure 20. The second tube 64 may then be removed. FIG. 4C shows that in this embodiment the second loop 42*a* ends up laced through the circumference of the support structure 20, however the second loop 42*a* may be laced through the support structure 20 in any manner that facilitates assembly of the valve device and positioning of the valve assembly 15 in the support structure 20. FIG. 4C also shows the support structure 20 placed and expanded so as to press the native valve leaflets 76 up against the aorta wall 82, however if the procedure so requires, native valve leaflets may be removed prior to placement and expansion of the support structure. Once the assembled valve device is in place at the site of implantation 70, the second pull wire 42 may be removed by pulling on one end. Alternatively, the second pull wire 42 may be tied and then cut.

First and second pull wires may comprise biodegradable material and be left in place and allowed to degrade. In the embodiment illustrated in FIGS. 4A-4C, the support structure 20 is placed and expanded after assembly of the valve sections 50*a*-50*c*, so as to minimize the time period during which the patient has no valve activity. However, in an alternative embodiment, the support structure 20 may be positioned prior to assembly of the valve sections into the valve assembly. For example, the support structure may be positioned using the second pull wire 42 and second tube 64 and then expanded, the second tube 64 is then preferably removed and the second pull wire 42 is left in place, and then the valve sections 50a-50c may be assembled into the valve assembly 15 using the first pull wire 41 and first tube 63. The valve assembly 15 may then be moved into position and assembled with the support structure 20 using the first and second pull wires 41, 42. These methods of valve assembly are applicable to modular valve devices comprising more than, or less than, the four modules illustrated in FIGS. 4A-4C, including modular valve devices comprising only valve sections as device modules, and such methods are well within the scope of the invention. For example, a modular valve device comprising two modules—i.e., a valve component and support structure—may be assembled using pull wires and tubes in a similar manner, which is well within the skill in the art in view of the above description. Where appropriate, more than two sets of pull wires may be used to assemble device modules. The skilled artisan can readily employ other assembly means similar to that described above and as described in co-pending U.S. application Ser. No. 12/686,338 (self-assembly), as desired.

Figure 5A:
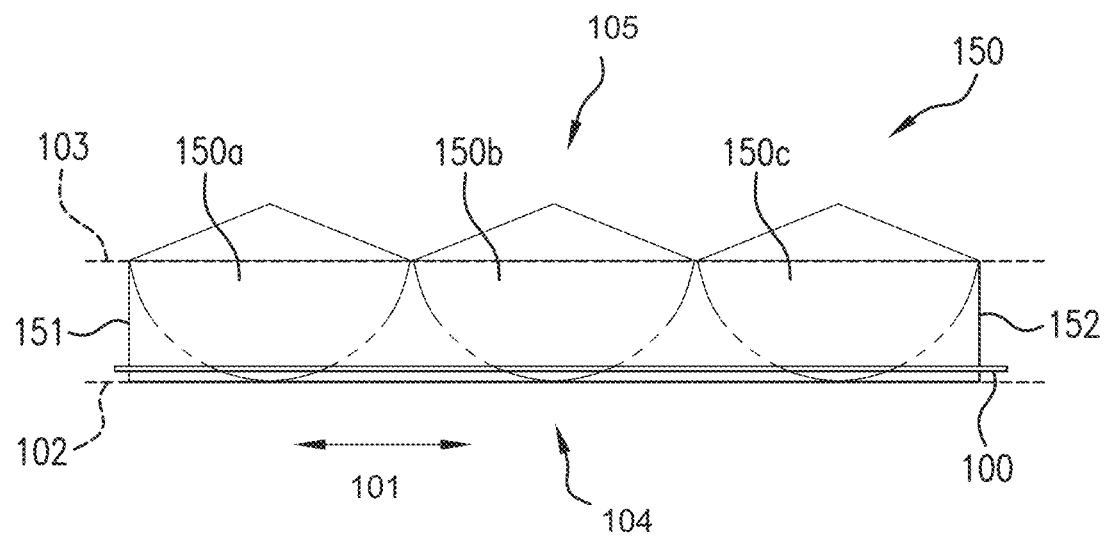
FIGS. 5A-C illustrate a valve module comprising a leaflets substructure, in an unassembled configuration (FIG. 5A), a delivery configuration (FIG. 5B), and assembled into a valve component (FIG. 5C).
Figure 5B:
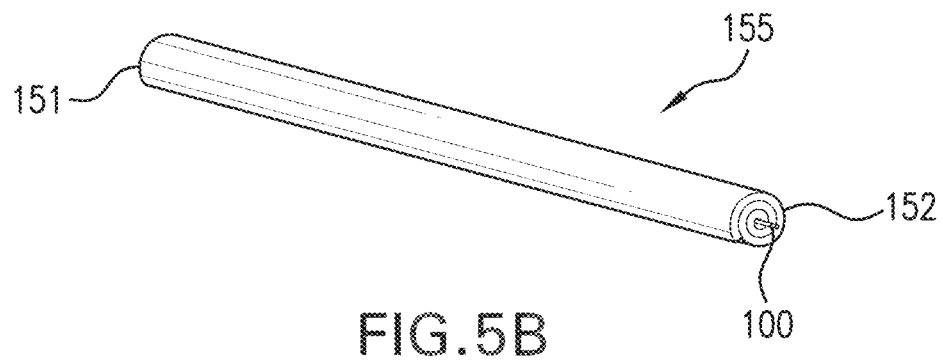
Figure 5C:
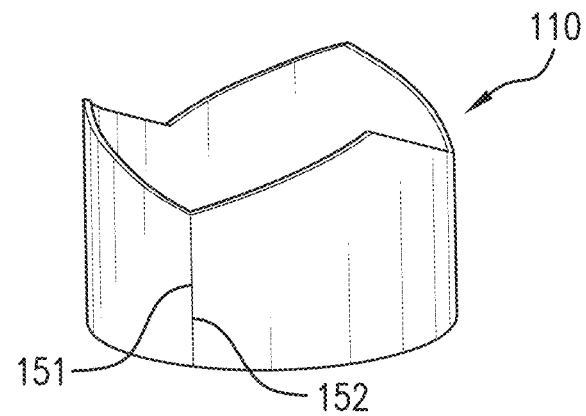

FIGS. 5A-5C depict an embodiment of a single-piece valve module that, unassembled, may comprise a leaflets substructure 150, which may be folded in a manner that minimizes the delivery diameter, i.e., its delivery configuration. Before loading the leaflets substructure 150 into the delivery system, it may be laid out in an unfolded, unassembled, substantially flat and generally rectangular or trapezoidal form, having a height axis, extending between a base 104 and an apex 105 (i.e., along the longitudinal axis of the assembled valve device), and a circumferential axis 101, as illustrated in FIG. 5A. In the embodiment depicted in FIGS. 5A-5C, the leaflets substructure 150 has three leaflets 150a-150c, but in other embodiments, the leaflets substructures may have 2 or more leaflets. The circumferential axis 101 of the leaflets substructure is commensurate with the circumference of the leaflets substructure in its assembled valve component configuration 110 (see FIG. 5C). A plastically deformable member 100 may be attached along a circumferential axis 101 of the leaflets substructure, so that, for example, in the unassembled state the plastically deformable 100 member may be attached along a base line 102 as illustrated in FIG. 5A, or along a commissural line 103 (not shown), or other circumferential line along the base-apex axis. Before loading into the delivery device, the leaflets substructure 150 may be rolled along its circumferential axis, either from base to apex, as illustrated in FIG. 5B, or from apex to base, with the first and second ends 151, 152 of the leaflets substructure 150 forming the ends of the cylindrically-shaped delivery configuration of the folded leaflets substructure 155.

After deployment of the folded leaflets substructure from the delivery device, the leaflets may be unfolded and assembled to form the 3-dimensional structure of the valve component, as illustrated in FIG. 5C. Unfolding of the leaflets substructure 155 from its delivery configuration may be assisted, for example, by a balloon-catheter, by pull wires and/or by push-rods, or by a combination thereof (not shown). In one embodiment, pull wires and/or push rods may be used to unroll the structure and to bring the first and second ends 151, 152 of the leaflets substructure 150 and the ends of the plastically deformable member 100, into a ring shape, e.g., a circle, ellipse, D-shape or any other shape appropriate for a valve module. In one such embodiment, the plastically deformable member 100 may be attached at the base line 102, the leaflets substructure 150 may be rolled along the circumferential axis 101 from base to apex, and the plastically deformable member 100 may be wrapped in the folded leaflets substructure 155 as illustrated in FIG. 5B. In this embodiment, one or more pull wires (not shown) may be threaded through base of the leaflets substructure 150 and wrapped with the folded leaflets substructure 155. The pull wires may be pulled to assist in unfolding the leaflets substructure 155 from its delivery configuration to its unassembled configuration 150, for example in conjunction with a tubular push-rod, similar to that depicted in FIGS. 4B-C. As one skilled in the art will recognize, one or more pull wires alternatively may be attached to one or more apices of the leaflets 150a-150c of the leaflets substructure 150 and wrapped in the folded leaflets substructure 155, for example in embodiments where the leaflets substructure is folded from apex to base (not shown).

To form the 3-dimensional valve component 110, in one embodiment for example, the first and second ends 151, 152 of the leaflets substructure 150 may be brought together, for example, using pull wires and/or push rods (not shown). For example, one end of the plastically deformable member 100 may have a pull wire attached to it (not shown) and the other end of the plastically deformable member 100 may have a loop through which the pull wire is threaded (not shown). The first and second end 151, 152 of the leaflets substructure similarly may have pull wires attached and threaded therethrough. A push-rod, for example a tubular push-rod similar to that described above in FIGS. 4B-C, may be used in conjunction with the one or more pull wires to pull the ends of the plastically deformable member 100 and leaflets substructure 150 together to form a tubular structure (not shown). A balloon-catheter then may be inserted through the tubular structure and inflated to expand the plastically deformable member 100 and leaflets substructure 150 into a ring-like shape to form the assembled valve component 110, i.e., a working configuration having a conduit, as depicted in FIG. 5C. The "ring-like shape" may be circular, elliptical, multi-lobular, D-shaped or any other appropriate shape for the valve device. Locking mechanisms may be provided to lock together the first end 151 to the second end 152, as described further below, either before expansion into the assembled configuration or after expansion into the assembled configuration.

Figure 6A:
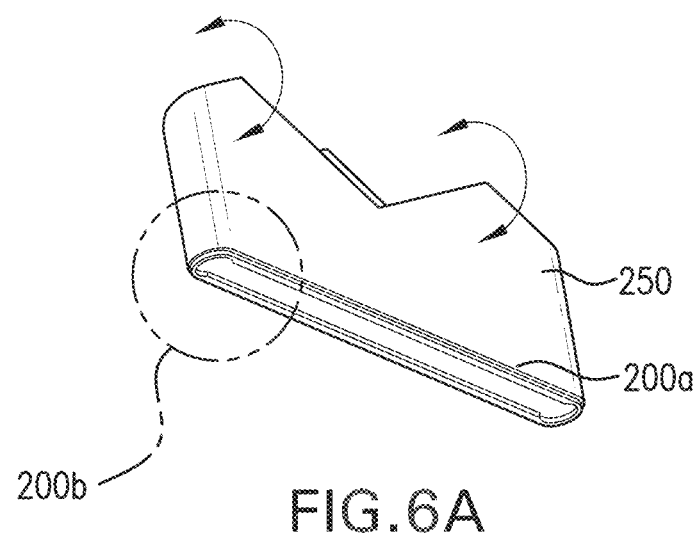
FIGS. 6A-C illustrate a valve module comprising a leaflets-ring, in an unassembled configuration (FIG. 6A), a delivery configuration (FIG. 6B), and assembled into a valve component (FIG. 6C).
Figure 6B:
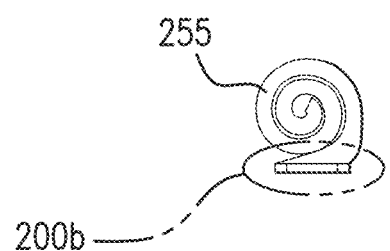
Figure 6C:
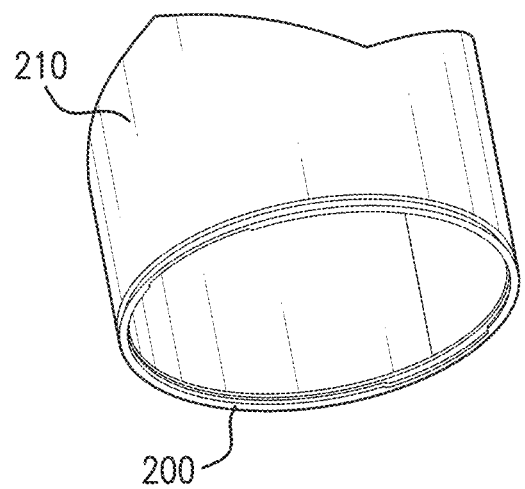

In another aspect of the embodiment of the single-piece valve module illustrated in FIGS. 6A-C, the valve module may be a ring of leaflets (leaflets-ring) 250. In this embodiment, the leaflets-ring 250 may have an unassembled configuration—a substantially flat two-ply structure, as illustrated in FIG. 6A. The leaflets-ring 250 may have a plastically deformable ring member 200 attached to or incorporated into, for example, the base of the valve module (see FIG. 6C). The leaflets-ring 250 has an unassembled configuration having a two-ply, substantially flat shape, as shown in FIG. 6A. When squashed to its substantially flat unassembled configuration, the leaflets-ring 250 has a length (or circumferential axis) and a width (or height). The plastically deformable ring member 200 in an unassembled configuration may have two substantially parallel long portions 200a and two bent ends 200b, as shown in FIG. 6A, which may hold the leaflets-ring 250 in its substantially flat, unassembled configuration. From its unassembled configuration, the leaflets-ring 250 may be folded into a delivery configuration 255 by rolling along the circumferential axis in the direction of its height, for example, from apex to base, as indicated by the arrows in FIG. 6A and as shown in FIG. 6B, or from base to apex.

Pull wires and/or push-rods (not shown) may be used to unroll the folded, unassembled leaflets-ring 255 from its delivery configuration. For example, in one embodiment (not shown), the apical portion of the leaflets-ring 250 may be connected to one or more pull wires, which may be rolled with the leaflets-ring 250 for delivery. The rolled leaflets-ring 255 may be unfolded by pulling the one or more pull wires. As one skilled in the art will recognize, one or more pull wires may alternatively be attached to the base of the leaflets-ring, for example where the leaflets-ring is rolled from base to apex, to assist in unfolding the rolled leaflets-ring 255 from its delivery configuration.

To form the 3-dimensional valve component 210, the unassembled plastically deformable ring member 200a, 200b is expanded, for example by balloon expansion, using push-rods and/or pull wires, or a combination thereof, thereby transforming the leaflets-ring 250 into an assembled valve component 210, i.e., a working configuration having a conduit, as depicted in FIG. 6C. In one embodiment, for example, a balloon-catheter (not shown) may be inserted through the unfolded, unassembled leaflets-ring 250 and inflated to expand the plastically deformable ring member 200 to a ring-like shape. The "ring-like shape" may be circular, elliptical, D-shaped or any other appropriate shape for the valve device. In one aspect of this embodiment (not shown), a string or pull wire may be pre-threaded through the leaflets-ring 250 with one end connected to the balloon-catheter to assist pulling the balloon catheter into the leaflets-ring 250. Once the leaflets-ring 250 has been assembled into the 3-dimensional valve component 210, the valve component 210 may be combined with and locked to a support structure (not shown) using locking mechanisms to form the assembled valve device. In an alternative embodiment, the leaflets-ring 250 may be assembled into the 3-dimensional valve component 210 within the support structure.

FIGS. 7-15 describe examples of locking mechanisms that may be used to secure or attach the device modules together after they have been combined or assembled.

FIGS. 7 and 7A illustrate one embodiment of locking mechanisms that may be suitable for attaching valve sections, e.g., 50a, 50b to each other to yield the valve assembly 15 shown in FIG. 2. Pull wires 40 may be used to pull the valve sections 50a, 50b together, so that the first side 51a of the first valve section 50a locks to the second side 52b of the second valve section 50b. FIG. 7A illustrates one embodiment of a locking mechanism. Each valve section may have a plurality of attachment points comprising, for example, a locking mechanism comprising male components 16 and female components 17. The male components 16 and female components 17 are positioned in such a manner that a male component 16 from one valve section will line up with a female component 17 of another valve section.

As specifically illustrated in FIG. 7A, for example, a first valve section 50a may comprise a plurality of male components 16 on a first side 51a that line up with a plurality of female components 17 on a second side 52b of a second valve section 50b. The male component 16 of the first valve section 50a locks into the female component 17 of another valve section 50b.

Where there are three valve sections, the second side 52a of the first valve section 50a may have a plurality of female components 17 that in turn line up with a plurality of male components 16 on the first side (not shown) of a third valve section (not shown), and the first side 51b of the second valve section 50b may have a plurality of male components 16 that in turn line up with a plurality of female components 17 on the second side (not shown) of a third valve section (not shown). Similar arrangements are possible for valve assemblies comprising 2, 4, 5 or more valve sections. The attachment points on the valve sections may be located along the lateral edges of the sections, as depicted in FIG. 7.

FIGS. 8A-C illustrate one embodiment of a locking mechanism for attaching a valve module and a support structure. In particular, as depicted in FIGS. 8A and 8B, the support structure 20 comprises a plurality of attachment points comprising hooks 21. The valve module 10 comprises a groove 22 along its proximal edge 12, as defined by the fluid flow in the lumen—the proximal edge 12 being the "upstream" edge. The hooks 21 of the support structure 20 fit into the groove 22 of the valve module 10, as shown in FIG. 8B, to secure the two modules together, as shown in FIG. 8C. The groove 22 may extend along the entire proximal edge 12 of the valve module 10 so that the hooks 21 can catch the groove 22 independently of the axial rotation of the valve module 10. Alternatively, the valve module 10 may have a plurality of short grooves spaced around the proximal edge 12 so as to be aligned with the hooks 21 of the support structure 20.

The support structure may be designed so that the valve sections may be connected thereto at various axial positions. For example, the support structure 20 may have several sets of hooks 21, spaced at intervals along the longitudinal axis, making available more than one attachment position in the proximal-distal direction. Such a design provides the clinician with flexibility in where the valve assembly may be placed within the support structure.

Figure 9:
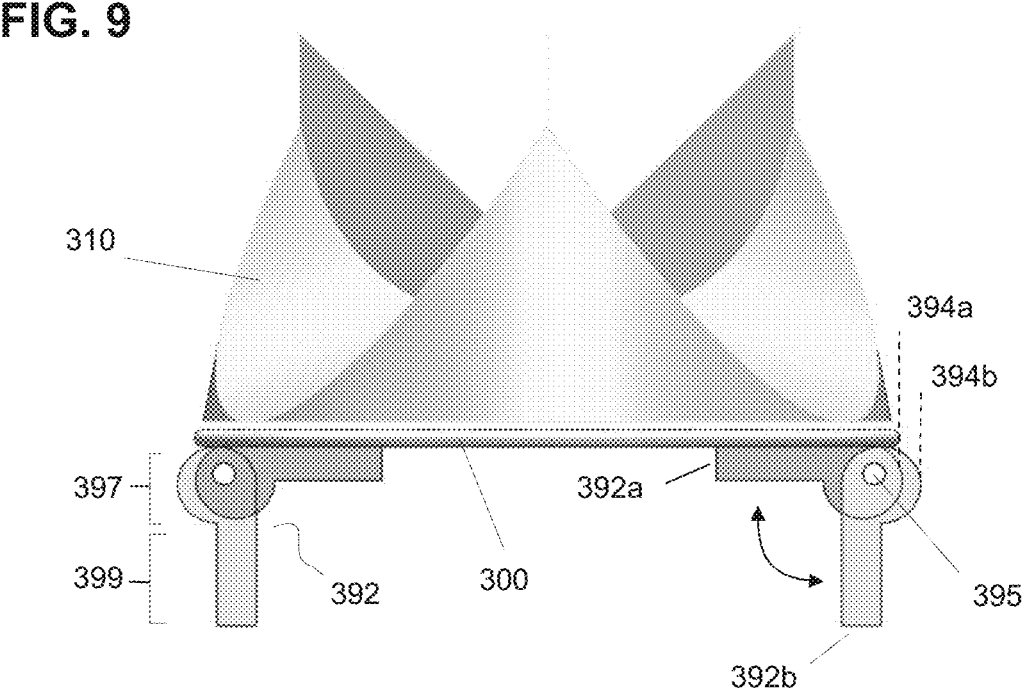
FIG. 9 illustrates an embodiment of a locking tab as an integral locking mechanism for attaching a valve module to a support structure.

FIG. 9 illustrates an embodiment of a locking tab 392 for attaching a valve module 310 to a support structure (not shown, for clarity). The locking tab 392 locks the device modules together by interference fit. The valve module 310 includes or is attached to a ring 300 and the locking tab 392 is attached to the ring 300. As depicted in FIG. 9, the locking tab 392 is connected to the valve module 310 at its base. After the valve module 310 and support structure have been combined, one or more locking tabs 392 may be operated to engage the support structure, so as to lock the valve module and support structure together. The embodiment of a locking tab 392 illustrated in FIG. 9 is an interference-fit lock mechanism using a component integral to the valve module that is rotationally operable between an unlocked position 392a and a locked position 392b about a pivot axis 395. Preferably, the valve module 310 has two or more locking tabs 392.

As FIG. 9 illustrates, the locking tab 392 has a pivoting end 397 and a swinging end 399 and operates by rotating between the unlocked position 392a, in which the swinging end 399 is oriented toward the middle of the valve module, and the locked position 392b, in which the swinging end 399 is oriented axially, i.e., parallel to the longitudinal axis of the valve device. The pivoting end 397 has a substantially circular shape and a pivot axis 395, around which the pivoting end 397 of the locking tab 392 rotates. As shown in FIG. 9, the pivot axis 395 is not centered within the substantially circular shape of the pivoting end 397, such that when in the unlocked position 392a, the lateral edge 394a of pivoting end 397 is substantially flush with the circumference of the valve module 310, whereas in the locked position 392b, the lateral edge 394b of pivoting end 397 extends beyond the circumference of the valve module 310 and exerts a radial force upon the support structure sufficient to lock the modules together by interference fit.

FIGS. 10A-D illustrate another embodiment of an integral locking mechanism, a stud-and-harbor lock. The stud-and-harbor lock may be used to attach a valve module to a support structure. In this embodiment, the valve module 410 has a ring 400 along its outer circumference. As shown in FIG. 10A, the ring 400 includes a plurality of studs 404 located on its outer surface at defined intervals around the circumference of the ring 400. The stud 404 fixedly protrudes outwardly from the outer surface of the ring 400. The support structure (not shown) comprises a plurality of posts 426 attached to it on its interior surface and oriented in an axial direction. The plurality of posts 426 are attached to the support structure at defined intervals around the inner circumference that match up with the studs 404 on the ring 400. Each post 426 includes on an interior surface a plurality of "harbors" 425 (for example, cut-out grooves). The harbor 425 is operable to receive the studs 404 in registering relation. Thus, the stud-and-harbor lock comprises a stud 404 located on a ring 400 to which the valve module 410 is attached that docks in a harbor 425 located on a post 426, which is attached to the support structure, thereby locking the valve module and support structure together.

A stud 404 on the ring 400 can be docked to a harbor 425 on a post 426 by rotating the valve module 410 relative to the support structure (not shown) such that the stud 404 aligns with the harbor 425 as shown in FIG. 10B, thereby attaching the two modules. The stud 404 and harbor 425 may lock together for example by interference-fit, magnetic attraction, ratchet, vertical ridge-channel, or other mechanism known in the art. Depending on the particular choice of attachment mechanism, the device modules may be locked and unlocked by rotating the valve module 410 in either direction, e.g., clockwise or counter-clockwise, as illustrated by a vertical channel-ridge mechanism in FIGS. 10C, 10C', 10D and 10D', or in an embodiment where the stud 404 and harbor 425 lock together by a ratchet mechanism, by rotating the valve module 410 in the one direction, e.g., clockwise.

As illustrated in FIGS. 10C and 10C', the stud 404 may have a vertical channel 408, and as illustrated in FIGS. 10D and 10D', the harbor 425 may have a vertical ridge 4328. FIG. 10C illustrates the channel 408 in the stud 404 on the ring 400 from a front view, and FIG. 10C' illustrates the channel 408 in the stud 404 from a top view. FIG. 10D illustrates the ridge 428 in the harbor 425 from a side view of the post 326, and FIG. 10D' illustrates the ridge 428 in the harbor 425 from a front view. The valve module 410 may be rotated until the vertical channel 408 in the stud 404 engages the vertical ridge 428 in the harbor 425 limiting further rotation of the valve module 410.

In a ratchet mechanism (not shown), the stud 404 and harbor 425 may be angled at supplementary angles to each other (for example, in a sawtooth pattern) such that the valve module will rotate in one direction, e.g., clockwise, because the front side of the stud 404 is smaller than the rear side. In this embodiment of a ratchet-type mechanism for the stud 404 and harbor 425, the valve module 410 may be locked by rotating it in one direction relative to the post 426, e.g., clockwise, until the harbor 425, adapted to be in registering relation with stud 404, holds it in place. At this point, due to the geometries of the stud and the harbor, they can be unlocked, if necessary, by rotating the valve module 410 in the same direction, e.g., clockwise, relative to the post. Rotation in the opposite direction, e.g., counter-clockwise, is hindered by the discontinuity in radius between ring 400 and the rear side of stud 404.

Figure 11A:
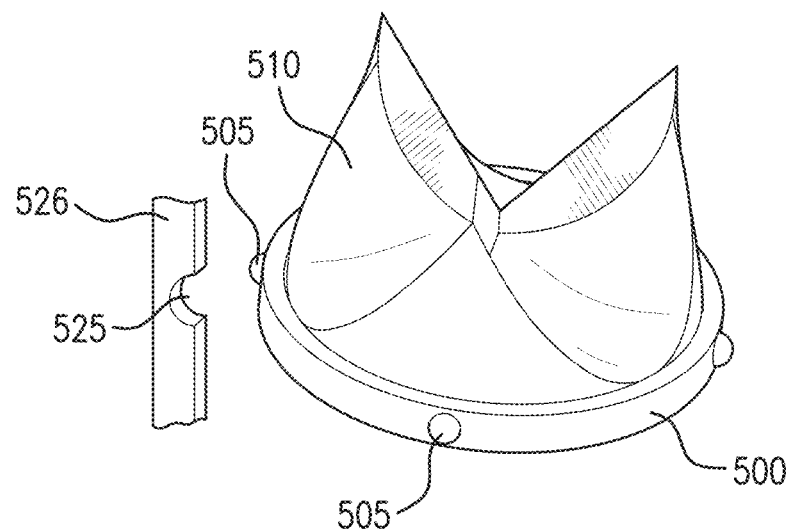
FIGS. 11A-B illustrate an embodiment of a quick-release locking mechanism for attaching a valve module to a support structure.
Figure 11B:
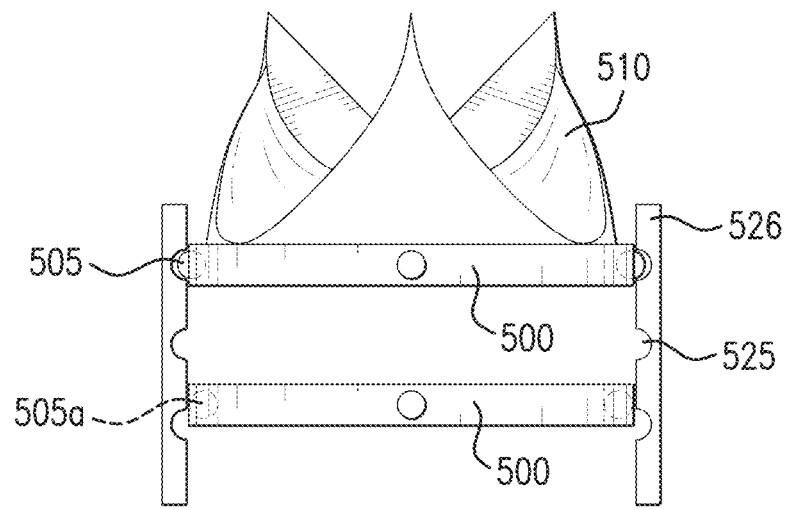

FIGS. 11A and 11B illustrate a quick-release button locking mechanism comprising a plurality of "buttons" 505 that lock into complementary "harbors" 525. As shown in FIG. 11A, the valve module 510 may be attached to or comprise a ring 500. The ring 500 includes a plurality of buttons 505 located on its outer surface at defined intervals around the circumference of the ring 500. The support structure (not shown, for clarity) comprises a plurality of posts 526 attached to it on its interior surface and oriented in an axial direction, as shown in FIG. 11B. The plurality of posts 526 are attached to the support structure at defined intervals around the inner circumference that match up with the buttons 505 on the ring 500. Each post 526 includes on an interior surface a harbor 525 (for example, a cut-out groove). As illustrated in FIG. 11B, the ring 500—and therefore the valve module 510 may be locked to the support structure (not shown) via button-harbor pairs—buttons 505 that comprise a quick release mechanism lock into harbors 525 on the plurality of posts 526 attached to the support structure. FIGS. 11A and 11B illustrate an embodiment in which the valve device includes four pairing positions where the valve module buttons and support structure harbors engage, however in other embodiments, the valve device may have three or as many as six or eight such pairing positions. In another embodiment, there may be for example two or three times as many buttons on the valve module ring as posts on the support structure (or vice versa) for ease of rotational positioning of the valve module relative to the support structure. In an alternative embodiment, the harbor member may comprise a groove ring on the interior surface of the support structure.

The quick release mechanism of the buttons 505 may include a spring, or a push or pull release mechanism, or any other appropriate configuration as would be apparent to the person skilled in the art. In one aspect of the embodiment depicted in FIGS. 11A and 11B, pulling or pushing a safety catch may activate or deactivate the quick release mechanism. For example, upon activation of the safety catch, the buttons 505 may be activated such that they protrude outwardly from the outer surface of the ring 500, thereby locking into the harbors 525 of the post 526. Similarly, upon deactivation of the safety catch, the buttons 505 are deactivated such that they retract from the harbors 525 to appear substantially even with the outer surface of the ring 500, thereby unlocking the valve member from the device frame. In an alternative aspect of this embodiment, the buttons 505 may be spring-loaded and activate and deactivate according to whether the spring is engaged or disengaged. The activated and deactivated buttons are depicted in FIG. 11B. Thus, with reference to a spring-based system, a button 505a facing a post 526 is restrained from protruding by the post 526, permitting the ring 500a to be moved axially along the post 526 until a harbor 525 is encountered. The button 505 facing a harbor 525 may freely protrude outward from the ring 500 and engage the harbor 525. Upon application of sufficient force, button 505a may be disengaged from the harbor 525, restrained by the post 526 and the ring 500 may be moved axially along the post again 525. The option of posts 526 having a plurality of harbors 525 also is depicted in FIG. 11B, which arrangement is useful for fine adjustment of the valve module 510 relative to the support structure, as described in detail in FIGS. 1a-1b and ¶28-29 of co-pending U.S. patent application Ser. No. 12/686,340 (adjustment), entitled "Method and Apparatus for Fine Adjustment of a Percutaneous Valve Structure," filed on date even herewith, which application is incorporated herein by reference.

Valve device modules may also be attached using a component separate from (i.e., not integral to) the device modules. Non-integral locking mechanisms are applicable to attaching valve sections together or attaching the valve module to the support structure. Thus, a separate component may be used as a locking mechanism for joining the device modules together, as illustrated by way of example for joining a valve module to the support structure as illustrated in FIGS. 12-14. The locking mechanisms of the invention that are not integral to the device modules, preferably are of the kind that are easily engaged from a remote location, yet also provide a secure fitting that will not disengage during use. Alternatively, the non-integral locking mechanisms may include a member attached to the valve module and/or support structure that prevents engagement until it is removed, for example a tab that prevents two components from engaging.

After the valve module(s) and support structure have been assembled and positioned, one or more components may be inserted percutaneously into the valve device and placed so as to lock the two modules together, for example, using a snap-fit mechanism, as illustrated in FIGS. 12A-12B. FIG. 12A illustrates one embodiment of a separate (non-integral) snap-fit locking mechanism, that uses a one piece snap-fit prong 692 comprising a leading end 692a and a base end 692b. Details of the snap-fit prong 692 are illustrated in FIG. 12A'. In the embodiment of FIG. 12A the valve module 610 may have a plurality of axial tabs 613 at or near its base, for example attached to a ring 600, at defined intervals around its circumference extending axially from the valve module 610. Each axial tab 613 includes a hole (not shown), each adapted to receive a snap-fit prong 692. Alternatively, the plurality of holes 611 may be located directly on the ring or the base of the valve module 610 (as illustrated in FIG. 12B). The support structure (not shown, for clarity) comprises a plurality of posts 626 attached to it on its interior surface and oriented axially. The plurality of posts 626 are attached to the support structure at defined intervals around the inner circumference that match up (i.e., in registering relation) with the valve module axial tabs 613. Each post 5626 includes post hole (not shown), which is also adapted to receive snap-fit prong 592, at the same axial level, so that when the valve module 510 and support structure are assembled, each post hole of the post 626 may be in register with the hole in the axial tab 613 of the valve module 610.

In another embodiment, as illustrated in FIG. 12B, the snap-fit mechanism is a two piece mechanism. The snap-fit prong 692 may be received by a snap-fit receptacle 693 on the opposite side of the second hole to interlock the intervening device components having integral holes through which the snap-fit prong may be disposed. In particular, FIG. 12B shows schematically how the base end 692b of the snap fit prong 692 may secure one device module, here the valve module 610, and the leading end 692a of the snap-fit prong 692 may extend through an integral hole 611 in the valve module 610 and an integral hole 627 in the support structure 620 and engage the snap-fit receptacle 693, thereby securing the valve module and the support structure. In another aspect of the two-piece snap-fit mechanism (not shown), the snap-fit prong 692 and snap-fit receptacle 693 may also be used with an axial tab 613 and post 626.

The snap-fit prong 692 may be disposed from within the assembled valve device to the exterior of the valve device, as illustrated in FIG. 12B, i.e., the leading end 692a passes first through the hole 611 in the valve module 610 and then the hole 627 in the support structure 620 post. Alternatively, the snap-fit prong 692 may be disposed from the outside of the valve device towards the center, as illustrated in FIG. 12A, passing first through the hole in the post 626 and then the valve module hole 611. In the latter case, the snap-fit prong 692 may be disposed through the valve module and support structure before the support structure is fully expanded and implanted in the location of implantation of the valve device.

The snap-fit locking mechanism may work in a similar fashion to one of the embodiments depicted in FIG. 12A or 12B, to attach the sides of valve sections together (not shown), e.g., to attach the first side of a first valve section to the second side of a second valve section, or to attach the sides of a leaflets substructure together. The snap-fit locking mechanism may also be an integral locking mechanism (not shown). For example, the snap-fit prong may be integral to the post of the support structure, in which case the base end is contiguous with the support structure. In this embodiment, the valve module may comprise holes or receptive space that is the structural equivalent of a snap-fit receptacle at intervals around its circumference that in register with each post and the lumenal end of the integral snap-fit prong may be disposed through the hole integral to the valve module or the integral receptive space in a manner useful to attach the two device modules. Alternatively, a snap-fit prong may be integral to the base of the valve module or a ring attached to the valve module and engage a hole integral to the support structure or a post attached to the support structure, or the post may include receptive space that is the structural equivalent of a snap-fit receptacle, for example on a post.

FIGS. 13A-13E illustrate interlocking geometries that are related to the non-integral snap-fit mechanism shown in FIGS. 12A-12B, but may be referred to as pins, pegs, rivets and stud-and-tube connectors. For example, FIG. 13A depicts a pin 792 mechanism that secures a first and second device module 718, 719 as a sandwich. The pin 792 mechanism of the invention comprises a leading end 792a and a base end 792b. The base end 792b preferably has a head that secures the base end 792b of the pin 792 on one side of the device module sandwich. The leading end 792a comprises two prongs 795a, 795b that are straight when the leading end 792a of the pin 792 is disposed through the first and second device modules 718, 719 and are made to bend so as to lay flat against the outer surface of the device module sandwich opposite the side the head of the base end 792b sits. As illustrated in FIG. 13B, the pin 792 may be disposed through a hole integral to the pin tab 713 extending off the base of the valve module 710 and a post hole 727 integral to a post 726 of the support structure (not shown for clarity). The pin tab 713 may be attached, for example, to a ring 700 on the valve module 710, which ring 700 may be, for example, a self-assembly member, a plastically deformable ring, or similar structure. In the embodiment depicted in FIG. 13B, the pin 792 is oriented to secure the device modules from the vessel side toward the lumenal side of the valve device, so that it may be disposed first through the post hole 727 and then through the valve module hole (not shown). A device for securing the pins then may be inserted into the valve device to bend the pin prongs 795a, 795b against the lumenal surface of the pin tab 713. Alternatively, the pin prongs 795a, 795b may be manufactured from a shape-memory material, with a preset bent configuration. A suitable device may include an inflatable balloon catheter. Alternatively, the pins may be disposed in the opposite direction through the first and second device modules 718,

719. In this case, the wall of the body lumen can serve to secure the pin by bending the pin prongs 795a, 795b.

FIGS. 13C-13E illustrate other possible geometries for embodiments using pins, pegs, rivets, and stud-and-tube connectors. In particular, FIG. 13C shows a peg 892 in accordance with the invention which may be used with a post hole or a valve module hole, FIG. 13D shows a rivet 992 in accordance with the invention which may be used with a post hole or a valve module hole, and FIG. 13E shows a stud-and-tube connector 1092 in accordance with the invention, which may be used with a post hole or a valve module hole. The device modules may also be manufactured so that structures equivalent to any of the peg, rivet and stud-and-tube connector locking mechanisms illustrated in FIGS. 13C-13E, or a structure similar to the pin illustrated in FIGS. 13A and 13B, are integral to the device components, so that the interlocking geometries need not be applied to the device components, which can simplify the locking procedure. Other varieties of interlocking geometries that may be integral locking mechanisms within the scope of the invention include dove-tail, rivet-type, and hook-and-eye-type. For example the stud-and-harbor mechanism may be designed with a dove-tail geometry.

In each of the above embodiments, the ring may be, for example, a collapsible but firm portion of the valve module that may be located at the base of the valve module, or a plastically deformable member as described herein. Alternatively, the ring may be a self-assembly member as described, for example, in ¶¶36-38, 45-46, 51-69 and FIGS. 2a-10 of co-pending U.S. patent application Ser. No. 12/686, 338 (self-assembly), filed on date even herewith, which application is incorporated herein by reference.

Figure 14A:
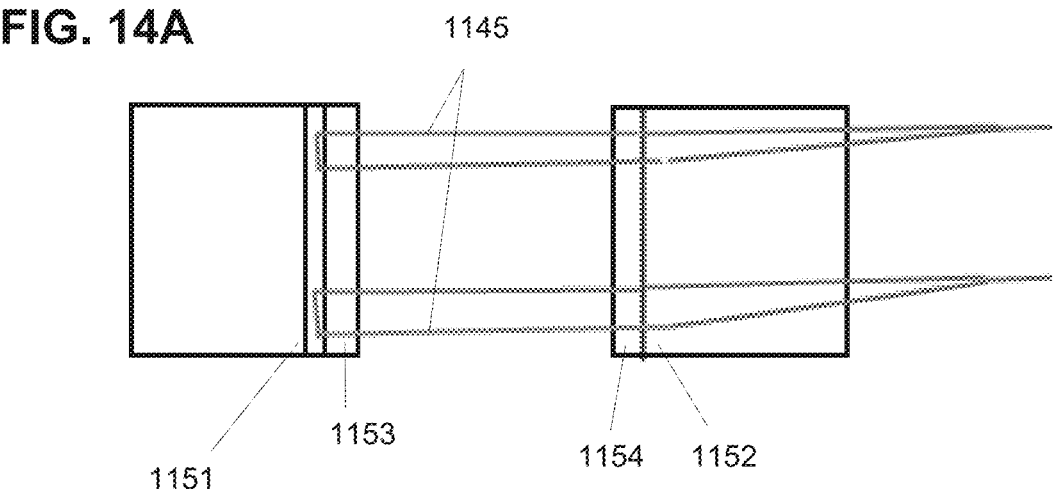
FIGS. 14A-C depict aspects of an embodiment of the interlocking curvilinear groove mechanism.
Figure 14B:
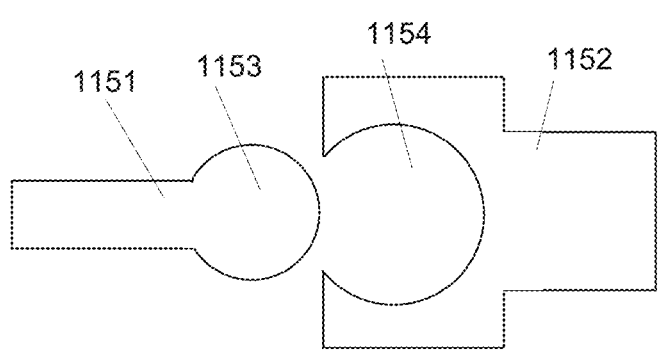
Figure 14C:
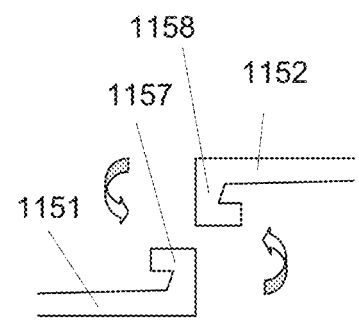
Figure 14C:
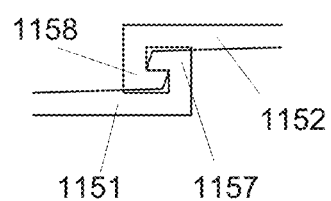

Another example of integral interlocking geometric mechanisms, is the interlocking curvilinear groove mechanism, also referred to in the art as a zip-lock mechanism, as depicted in FIGS. 14A-14C, which is particularly useful for attaching together the edges of valve sections or the edges of a leaflets substructure. In one aspect of this embodiment, the interlocking curvilinear groove mechanism may be a sliding interlocking curvilinear groove mechanism.

As illustrated in FIGS. 142A-C, a first side 1151 and a second side 1152 of a valve module may be locked together via an interlocking curvilinear groove mechanism because the first side 1151 comprises a geometric shape capable of interlocking in registered relation with the second side 1152. As shown in FIG. 14A, the first side 1151 and second side 1152 of the valve module may be guided toward each other using strings 1145 or wires, that are threaded through the first side 1151 and second side 1152. The strings 1145 may be pull wires, as described in FIGS. 4A-4C. The first side 1151 may have an edge having a bulbous cross-section 1153, which bulbous edge 1153 may have a rounded, for example substantially circular, shape as illustrated in FIG. 14B, but may also be rectangular (including square), triangular, or any other appropriate geometric shape, for example as illustrated in FIGS. 14C and 14C'. The second side 1152 of the valve module may a complementary receptive tract edge 1154 having a cross-section adapted to be in registering relation with the shape of the cross-section of the bulbous edge 1153 of the first side 1151. Thus, for example, where the bulbous edge 1153 of the first side 1151 is substantially rounded or circular, as illustrated in FIG. 14B, the receptive tract edge 1154 of the second side 1152 has a complementary circular cross-section, into which the bulbous edge 1153 of the first side 1151 engage or mate by interlocking and interference fit. This locking mechanism is referred to as an interlocking curvilinear groove mechanism, because as illustrated in FIG. 14A, the bulbous edge 1153 and receptive tract edge 1154 preferably each comprise strips extending along the entire contacting portions first and second sides 1151, 1152 of the valve module. Thus, the bulbous edge 1153 may be substantially cylindrical, for example, in an embodiment where the cross-section is substantially circular, and the receptive tract edge 1154 may be a substantially cylindrical groove.

In another aspect of the interlocking curvilinear groove mechanism, as illustrated in FIG. 14C, the first side 1151 may have a first hook shaped edge 1157 and the second side 1151 may have a second hook shaped edge 1058, which first and second hook edges 1157, 1158 are capable of interlocking and holding by tight fit, or interference fit, as illustrated in FIG. 14C'.

In one aspect of this interlocking curvilinear groove mechanism, or zip-lock, embodiment, where the valve module in an unassembled configuration is a single-piece leaflets substructure, as described, for example, with respect to FIG. 5A-C, as well as the leaflets substructure comprising a self-assembly member as described in ¶¶52-53 and FIG. 2a-2c and at of co-pending U.S. application Ser. No. 12/686, 338 (self-assembly), the above-illustrated first side 1151 and second side 1152 having interlocking edge geometries may be the first and second sides of the leaflets substructure. In this aspect of the zip-lock embodiment, a push rod and/or pull wires or guiding strings may be used to begin the process of bringing into registering relationship the bulbous first edge and the complementary receptive tract of the second edge of the leaflets substructure.

In another aspect of the interlocking curvilinear groove mechanism, or zip-lock, embodiment, where the valve module comprises a plurality of valve sections, as described, for example, with respect to FIGS. 2-4C above, as well as the valve sections comprising a self-assembly member as described in ¶¶48-51 and FIG. 1a-d of co-pending U.S. application Ser. No. 12/686,338 (self-assembly), the above-illustrated first side 1151 and second side 1152 having interlocking edge geometries may be the first side of a first valve section and the second side of an adjacent second valve section. Thus, by way of illustration for a valve module comprising three valve sections, the linear interference-fit mechanism may operate as follows. The first side of a first valve section may have a bulbous edge that mates with the receptive tract of the second side of a second valve section by fitting into the receptive tract of the second side of a second valve section in registering relationship. The edges of each valve section may be pulled together for example by wires 1145, such as for example pull wires or string, threaded through the edges, as illustrated in FIG. 14A, or by action of a self assembly member. Push-rods may be used in conjunction with the pull wires or string. The linear interference-fit may begin either at the proximal end or the distal end of the valve assembly. In a similar fashion, the first side of the second valve section may have a bulbous edge that mates with the receptive tract of the second side of a third valve section, and the first side of the third valve section may have a bulbous edge that mates with the receptive tract of the second side of the first valve section second edge. Similar arrangements are within the skill in the art for valve modules having two valve sections or more than three valve sections, in view of the description herein.

In the embodiment illustrated in FIGS. 14A and 14B, the linear interference-fit locking mechanism comprises mating edges of the first and second sides of a valve module. However in another zip-lock-type embodiment, applicable to either a leaflets substructure or a plurality of valve sections, the interlocking curvilinear groove mechanism may be between facing surfaces of the first and second sides 1151, 1152, for example an inner surface of the first side 1151 and an outer surface of the second side 1152, the facing surfaces located close to the edges of the first and second sides 1151, 1152. The interlocking geometries may attach by interference fit, in a manner similar to that illustrated, for example in FIGS. 6, 7, and col. 3, ll. 31-37 of U.S. Pat. No. 5,540,366, and FIGS. 2, 3 and col. 1, ll. 31-36 of U.S. Pat. No. 2,039,887, which are incorporated herein by reference. In one aspect, the locking mechanism may be a sliding zip-lock mechanism, in which embodiment the bulbous edge 1153 or first hook edge 1157 of the first side 1151 and receptive tract edge 1154 or second hook edge 1158 of the second side 1152, or interlocking facing surfaces, may be made to engage or mate by a device that slides along the edges to bring the complementary geometrical structures into a registering relationship, like a slider zip-lock arrangement.

An embodiment of an interference-fit locking mechanism useful for attaching a valve module to a support structure, in particular where the valve module includes a self assembly member having preset ring configuration, is described in detail in FIGS. 7 and ¶60 of co-pending U.S. application Ser. No. 12/686,338 (self-assembly), filed on date even herewith, which application is incorporated herein by reference. Briefly, the valve module may have attached to or threaded through it a self-assembly member, for example a ring or band, capable of reverting from a delivery configuration to a preset ring configuration. The support structure may have a groove or similar structure capable of receiving the ring or band as it presses outward to its preset configuration, thereby locking the valve module to the support structure by interference fit.

Figure 15:
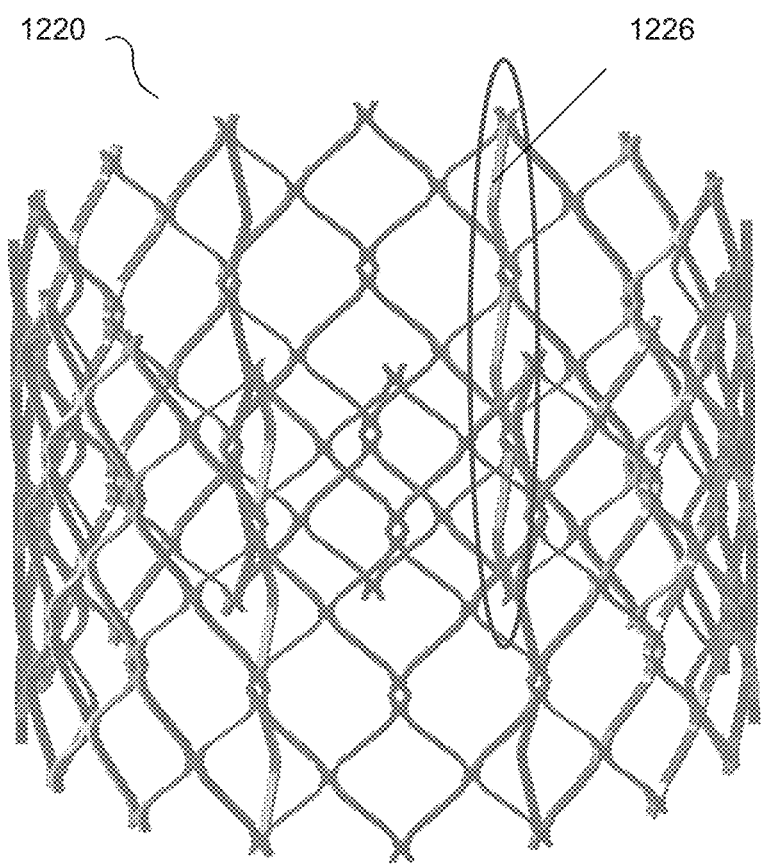
FIG. 15 illustrates a post attached to a support structure.

FIG. 15 illustrates a post 1226 attached to a support structure 1120. Specifically, FIG. 15 depicts how a post in accordance with any of the embodiments of FIGS. 9-13 may be attached to a frame or support structure without interfering with the expandability of the structure. Preferably the post is sufficiently flexible to not unduly interfere with the axial flexibility of the support structure but sufficiently radially rigid to function as needed in the particular embodiment in which it is used. Posts may be manufactured of the same material as the valve frame or a comparable material that does not chemically interact with the material of the valve frame. In any of the embodiments of FIGS. 9-13, the "posts" may be substituted by grooves, for example, cut out of a ring on the support structure. Harbors and post holes, as described for the embodiments of FIGS. 10-13, may be indentations or holes in the groove.

The locking mechanisms may be any fittings, preferably of the kind that is easily engaged from a remote location, yet also provides a secure fitting that will not disengage during use. The skilled artisan will readily recognize the interchangeability of different locking mechanisms and their application herein.

In any of the embodiments, it is possible and may be desirable to connect the valve module to the support structure adjustably so as to allow the final accurate positioning of the valve module. Thus, for example, the valve assembly may be connected to the support structure in an adjustable manner that will allow final adjustments of position of the valve assembly relative to the support structure after implantation of the valve device. Mechanisms for adjusting the position of the valve module relative to the support structure are described in detail in ¶¶21-24, 28-39 and FIGS. 1a-7 of co-pending U.S. patent application Ser. No. 12/686,340, entitled "Method and Apparatus for Fine Adjustment of a Percutaneous Valve Structure", filed on date even herewith, which application is incorporated herein by reference. The support structure also may be adjustably connected to the vessel wall.

In embodiments where a temporary valve is used, the temporary valve may be placed at the site of permanent valve implantation or at a position removed from the site of permanent valve implantation. As illustrated by way of example FIG. 16, in an aortic valve replacement, the temporary valve may be placed in the ascending aorta, proximal (downstream) of the location of implantation of the modular valve device. This arrangement may be useful in procedures where the modular valve is delivered via the apical approach (i.e., introducing the device from the ventricular side of the coronary valve). See, e.g., Singh, I. M. et al., "Percutaneous treatment of aortic valve stenosis," CLEVE. CLIN. J. MED. 75(11):805-812 (2008). However, circumstances may equally favor placing the temporary valve proximal of the location of implantation when the retrograde approach (i.e., introducing the device from the arterial side of the coronary valve) is used.

Figure 16:
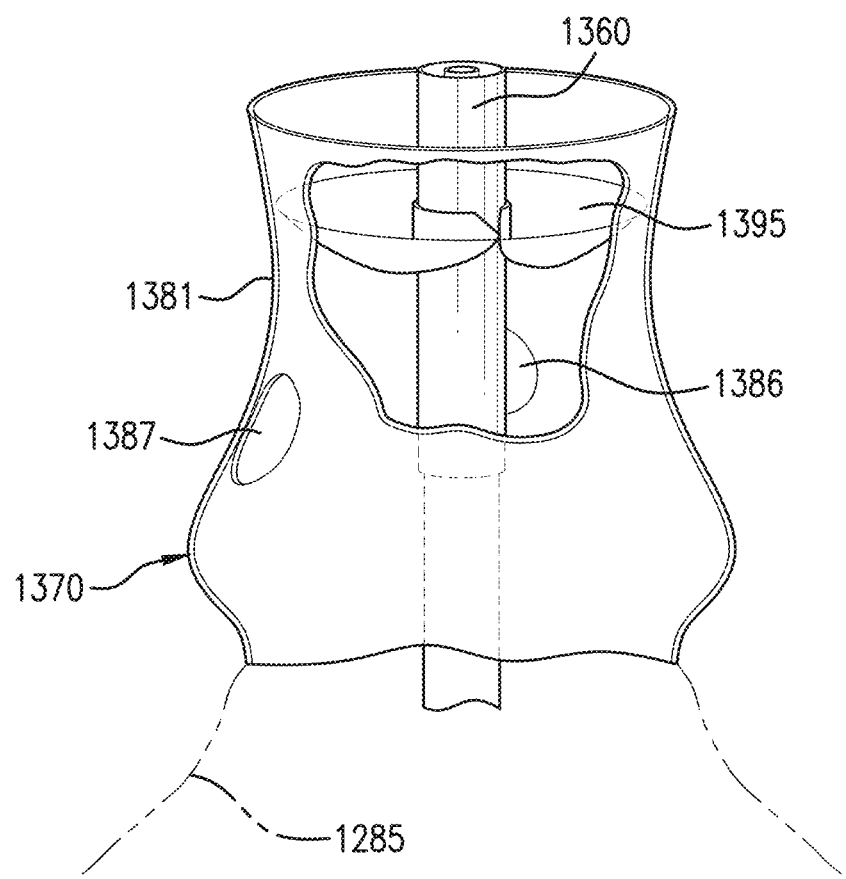
FIG. 16 illustrates an embodiment of a temporary valve as part of a delivery system, in accordance with the invention.

One embodiment of the temporary valve of the invention is depicted in FIG. 16. In this embodiment, the temporary valve 1395 is a single piece construction and is coextensive with the delivery system, in this case a catheter 1360, however the temporary valve may be constructed of two or more pieces. An advantage of having the temporary valve coextensive with or attached to the delivery system is that it may be readily removed when the delivery system is removed. The catheter 1360 to which the temporary valve 1395 is attached may be advanced to approximately the position where the modular valve device will be implanted, in this embodiment in the aorta 1381 at a position distal of the coronary ostia 1386, 1387, and the temporary valve 1395 may be triggered to expand automatically, like an inverted umbrella, using, for example, a shape memory wire. In an alternative embodiment (not shown), the temporary valve may comprise two pieces, and be designed so that the device modules may be passed through the temporary valve to the site of implantation. In an alternative embodiment, the temporary valve may be detached from the delivery device but connected by pull wires, which may be used pull the temporary valve out of the aorta when it is no longer needed.

Where the temporary valve is installed at the target site and the device modules are to be assembled remotely from the site of implantation, the delivery device may be retracted after installation of the temporary valve for deployment of the device modules of the permanent valve. Where the temporary valve is installed at the target site, the support structure may be implanted before the temporary valve, either (1) via a separate catheter using an opposite percutaneous approach from the delivery device carrying the temporary valve, or (2) by deploying the support structure from the delivery device in advance of deploying the temporary valve.

Figure 17:
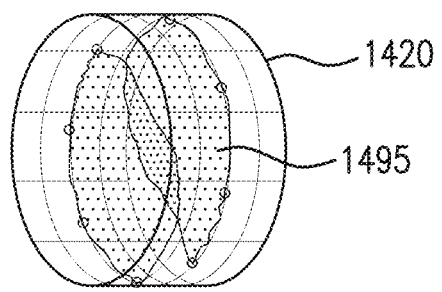
FIG. 17 illustrates an embodiment of a temporary valve attached to and delivered with a support structure.

In another embodiment, depicted in FIG. 17, the temporary valve may be attached to the support structure, and delivered and deployed and expanded with the support structure. The temporary valve 1495 may be attached to the support structure 1420 by stitching, gluing or similar means known in the art for pre-assembled percutaneous valves, or by detachable means. Thus, for example, the temporary valve 1495, in this embodiment depicted as a two piece structure, is attached to the support structure 1420 prior to compressing the support structure 1420 and mounting in the delivery device (not shown). As illustrated in FIG. 17, when the support structure 1420 is expanded, the temporary valve 1495 is deployed and controls blood flow until the valve portion of the modular valve device (not shown) is combined with the support structure 1420. The temporary valve 1495 in this embodiment may be used with either a self-expanding or balloon expandable support structure. In the latter case, for delivery the temporary valve may be attached to the support structure and then mounted on a balloon catheter. In the embodiment depicted in FIG. 17, the temporary valve 1495 is not removed, but may be crushed or otherwise degraded when the valve module(s) is combined with the support structure 1420. In an alternative embodiment, such a temporary valve 1495 may be removed just before the assembled valve module is deployed or after the assembled valve module is attached to the support structure.

It is important that a prosthetic valve device is placed in a vessel (or lumen) with precision to ensure proper valve function and safety to the patient. Accordingly, the device and system of the invention, as well as the method of delivering the device, may be used in conjunction with the placement system and method of placing a modular device that are described in ¶¶67-82 and FIGS. 7a-8 of priority U.S. application 61/144,007, and in ¶¶1a-2 and FIGS. 24-42 of co-pending U.S. application Ser. No. 12/686,337 (placement), entitled "A System and Method for Placing a Percutaneous Valve Device," filed on date even herewith, which applications are incorporated herein by reference. As described in U.S. priority application No. 61/144,007 and co-pending U.S. application Ser. No. 12/686,337 (placement), the method of placing a prosthetic valve device in a body lumen with improved accuracy comprises, for example, affixing an anchor in a body lumen at a location of implantation of the permanent valve; and using said anchor to guide said prosthetic valve device to said location of implantation. The placement system comprises the valve device, delivery device and an anchor. Anchors may include a button or rivet-type device, a hook, a percutaneously-inserted leading suture, interconnecting geometries, or any other type of docking apparatus device. The system may further comprise placement wires connected to the anchors. In embodiments where an anchor is connected to a placement wire, the method may further comprise threading said placement wire through said valve device; loading said valve device into a delivery device so that free ends of said placement wires exit a proximal end of said delivery device; and guiding said device toward said anchor along said placement wire. In embodiments where the anchor comprises a leading suture, the method may further comprise threading said leading suture through said valve device; loading said valve device into a delivery device. Methods of placing a valve device in a lumen encompass employing other types of anchors.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:

1. A method of assembling a modular percutaneous valve device using a system comprising a percutaneous delivery device containing a plurality of device modules, including an expandable support structure and a valve module comprising a leaflets substructure having a flattened unassembled generally rectangular or trapezoidal form which is folded into a delivery configuration, said support structure having a compressed, unexpanded delivery configuration spatially separate from said valve module, wherein said device modules are assembled into said valve device after deployment from said delivery device to form a deployed configuration valve device, the method comprising:
   deploying said device modules from said delivery device to form an expanded support structure;
   unfolding said valve module to form a working configuration valve component; and
   combining said expanded support structure and working configuration valve component to form said valve device.

2. The method of claim 1, wherein said working configuration valve component is formed outside said support structure.

3. The method of claim 1, wherein said system further comprises one or more pull wires, said one or more pull wires connecting said device modules; said assembling step further including:
   forming said working configuration valve component using said pull wires.

4. The method of claim 1, wherein said system further comprises push-rods; said method further comprising:
   combining said device modules using said push rods.

5. The method of claim 1 or 3, wherein said system further comprises push-rods; said method further comprising:
   forming said working configuration valve component using said push rods.

6. A method of assembling a modular prosthetic percutaneous valve device into a unitary valve, said valve device comprising a plurality of device modules, said device modules including an expandable support structure and a valve module comprising a leaflets substructure having a flattened assembled generally rectangular or trapezoidal form which is folded into a delivery configuration, said support structure and said valve module each having a compressed, unexpanded delivery configuration spatially separate from the other prior to delivery, said method comprising:
   deploying said device modules to form an expanded support structure;
   pulling a pull wire connecting the support structure to the valve module, said pulling causing the valve module to move distally into the expanded support structure; and
   combining said expanded support structure and said valve module to form said unitary valve device.

7. The method of claim 6, wherein the valve module and support structure are delivered in tandem.

8. The method of claim 6, further comprising the step of adjusting a position of the valve module within the support structure via said pull wire.

9. The method of claim 6, wherein the pull wire is threaded through the valve module and support structure.

10. The method of claim 6, wherein the device modules are assembled into said valve device after deployment from a percutaneous delivery device.

11. The method of claim 6, wherein both free ends of the pull wire are pulled to move the valve module into the support structure.

12. The method of claim 6, further comprising the step of locking the valve module to the support structure.

13. The method of claim 6, further comprising the step of pulling one free end of the pull wire for removal.

14. The method of claim 6, wherein said valve module in said delivery configuration has a reduced outer profile.

* * * * *